United States Patent
Mao

(10) Patent No.: US 9,402,880 B2
(45) Date of Patent: Aug. 2, 2016

(54) TREATMENT FOR BONE FORMATION DISORDERS BY GROWTH FACTOR DELIVERY

(71) Applicant: The Trustees of Columbia University in the City of New York, New York, NY (US)

(72) Inventor: Jeremy J. Mao, Closter, NJ (US)

(73) Assignee: The Trustees of Columbia University in the City of New York, New York, NY (US)

( * ) Notice: Subject to any disclaimer, the term of this patent is extended or adjusted under 35 U.S.C. 154(b) by 155 days.

(21) Appl. No.: 13/785,947

(22) Filed: Mar. 5, 2013

(65) Prior Publication Data

US 2014/0072637 A1 Mar. 13, 2014

Related U.S. Application Data

(63) Continuation of application No. 12/439,669, filed on Oct. 14, 2009, now abandoned, which is a continuation-in-part of application No. PCT/US2007/018667, filed on Aug. 22, 2007.

(60) Provisional application No. 60/824,070, filed on Aug. 30, 2006.

(51) Int. Cl.
| | |
|---|---|
| *A61K 38/18* | (2006.01) |
| *A61K 9/50* | (2006.01) |
| *A61K 31/7088* | (2006.01) |
| *A61K 35/00* | (2006.01) |
| *A61K 35/33* | (2015.01) |
| *A61K 45/06* | (2006.01) |

(52) U.S. Cl.
CPC . *A61K 38/18* (2013.01); *A61K 9/50* (2013.01); *A61K 31/7088* (2013.01); *A61K 35/00* (2013.01); *A61K 35/33* (2013.01); *A61K 38/1825* (2013.01); *A61K 38/1841* (2013.01); *A61K 38/1866* (2013.01); *A61K 38/1875* (2013.01); *A61K 45/06* (2013.01)

(58) Field of Classification Search
None
See application file for complete search history.

(56) References Cited

U.S. PATENT DOCUMENTS

| | | | |
|---|---|---|---|
| 4,913,903 | A | 4/1990 | Sudmann et al. |
| 5,408,040 | A | 4/1995 | Grotendorst et al. |
| 5,837,258 | A | 11/1998 | Grotendorst |
| 6,358,741 | B1 | 3/2002 | Schmidt et al. |
| 6,492,129 | B1 | 12/2002 | Grotendorst |
| 6,531,146 | B2 | 3/2003 | Calhoun et al. |
| 6,673,362 | B2 | 1/2004 | Calhoun et al. |
| 2004/0146561 | A1 | 7/2004 | Sakurai et al. |
| 2005/0002915 | A1 | 1/2005 | Atala et al. |

FOREIGN PATENT DOCUMENTS

| | | |
|---|---|---|
| WO | WO 00/27868 | 5/2000 |
| WO | WO 00/35939 | 6/2000 |
| WO | WO 01/55210 | 8/2001 |
| WO | WO 02/081745 | 10/2002 |

OTHER PUBLICATIONS

Alhadlaq et al., Mesenchymal Stem Cells: Isolation and Therapeutics, Stem Cells Dev., 2004, pp. 436-448, vol. 13.
Altman et al., Cell differentiation by mechanical stress, FASEB J., 2002, pp. 270-272, vol. 16.
Butler et al., Functional Tissue Engineering Parameters toward Designing Repair and Replacement Strategies, Clin. Orthop. Relat. Res., 2004, pp. S190-S199, No. 427S.
Caplan, Mesenchymal Stem Cells: Cell-Based Reconstructive Therapy in Orthopedics, Tissue Eng., 2005, pp. 1198-1211, vol. 11, No. 7/8.
Chong et al., Rescue of Coronal Suture Fusion Using Transforming Growth Factor-β 3 (Tgf-β3) in Rabbits with Delayed-Onset Craniosynostosis, Anat. Rec. A. Discov. Mol. Cell Evol. Biol., 2003, pp. 962-971, vol. 274A.
Collins et al., Expression of matrix metalloproteinase genes in the rat intramembranous bone during postnatal growth and upon mechanical stresses, J. Biomech., 2005, pp. 485-492, vol. 38.
Giachelli, Ectopic Calcification: Gathering Hard Facts about Soft Tissue Mineralization, American Journal of Pathology, 1999, pp. 671-675, vol. 154, No. 3.
Hankemeier et al., Modulation of Proliferation and Differentiation of Human Bone Marrow Stromal Cells by Fibroblast Growth Factor 2: Potential Implications for Tissue Engineering of Tendons and Ligaments, Tissue Eng., 2005, pp. 41-49, vol. 11, No. 1/2.
Hong et al., Tissue-Engineered Rabbit Cranial Suture from Autologous Fibroblasts and BMP2, J. Dent. Res., 2004, pp. 751-756, vol. 83, No. 10.
International Search Report and Written Opinion dated Aug. 25, 2008 in related PCT Application No. PCT/US07/18667, filed Aug. 22, 2007, 7 pages.
Kopher et al., Suture Growth Modulated by the Oscillatory Component of Micromechanical Strain, J. Bone Miner. Res., 2003, pp. 521-528, vol. 18, No. 3.
Levy et al., Localized adenovirus gene delivery using antiviral IgG complexation, Gene Ther., 2001, pp. 659-667, vol. 8.
Liu et al., Simultaneous Detection of Multiple Bone-Related mRNAs and Protein Expression during Osteoblast Differentiation: Polymerase Chain Reaction and Immunocytochemical Studies at the Single Cell Level, Dev. Biol., 1994, pp. 220-234, vol. 166.
Lu et al., TGF-β1 Release from Biodegradable Polymer Microparticles: Its Effects on Marrow Stromal Osteoblast Function, J. Bone Joint Surg. Am., 2001, pp. S1-82-S1-91, Suppl. 1, vol. 83-A, Part 2.

(Continued)

*Primary Examiner* — Gregory S Emch
(74) *Attorney, Agent, or Firm* — Dentons US LLP

(57) ABSTRACT

It has been discovered that that certain growth factors can delay the ossification of a tissue site, such as a cranial suture, via the promotion of fibroblast differentiation and/or inhibition of osteoblast differentiation. Provided herein are methods for treating bone formation conditions or disorders, such as synostotic conditions, or ectopic mineralization conditions, via administration of compositions comprising connective tissue growth factor (CTGF), and optionally other growth factors or fibroblast or progenitor cells, to a tissue site of a subject in need thereof.

20 Claims, 24 Drawing Sheets

(56) References Cited

OTHER PUBLICATIONS

Mao, Calvarial development: cells and mechanics, Curr. Opin. Orthop., 2005, pp. 331-337, vol. 16.

Marion et al., Borate Glass Supports the in Vitro Osteogenic Differentiation of Human Mesenchymal Stem Cells, Mech. Adv. Materials Struct., 2005, pp. 1-8, vol. 12.

Mcknight et al., Resequencing of the characterised CTGF gene to identify novel or known variants, and analysis of their association with diabetic nephropathy, J. Hum. Genet., 2006, pp. 383-386, vol. 51.

Moioli et al., Sustained Release of TGFß3 from PLGA Microspheres and Its Effect on Early Osteogenic Differentiation of Human Mesenchymal Stem Cells, Tissue Eng., 2006, pp. 537-546, vol. 12, No. 3.

Mooney et al., Cytokine therapy for craniosynostosis, Expert Opin. Biol. Ther., 2004, pp. 279-299, vol. 4, No. 3.

Moreau et al., Growth factor induced fibroblast differentiation from human bone marrow stromal cells in vitro, J. Orthop. Res., 2005, pp. 164-174, vol. 23.

Moss, Growth of the Calvaria in the Rat, The Determination of Osseous Morphology, Am. J. Anat., 1954, pp. 333-361, vol. 94, No. 3.

Moussad et al., Connective Tissue Growth Factor: What's in a Name?, Mol. Gen. Metab., 2000, pp. 276-292, vol. 71.

Opperman et al., Transforming growth factor-ß3 (Tgf-ß3) down-regulates Tgf-ß receptor type I (Tßr-I) during rescue of cranial sutures from osseous obliteration, Orthod. Craniofacial Res., 2002, pp. 5-16, vol. 5.

Opperman et al., Cranial Sutures Require Tissue Interactions with Dura Mater to Resist Osseous Obliteration in Vitro, J. Bone Miner. Res., 1995, pp. 1978-1987, vol. 10, No. 12.

Rahaman et al., Stem Cell-Based Composite Tissue Constructs for Regenerative Medicine, Biotechnol. Bioeng., 2005, pp. 261-283, vol. 91, No. 3.

Rengel et al., High efficiency entrapment of superoxide dismutase into mucoadhesive chitosan-coated liposomes, Eur. J. Pharm. Sci., 2002, pp. 441-448, vol. 15.

Sakiyama-Elbert et al., Development of growth factor fusion proteins for cell-triggered drug delivery, FASEB J., 2001, vol. 15, 17 pages.

Teng et al., Functional recovery following traumatic spinal cord injury mediated by a unique polymer scaffold seeded with neural stem cells, Proc. Natl. Acad. Sci. U.S.A., 2002, pp. 3024-3029, vol. 99, No. 5.

Varde et al., Microspheres for Controlled Release Drug Delivery, Expert Opin. Biol. Ther., 2004, pp. 35-51, vol. 4, No. 1.

Whittlesey et al., Delivery systems for small molecule drugs, proteins, and DNA: the neuroscience/biomaterial interface, Experimental Neurology, 2004, pp. 1-16, vol. 190.

Yao et al., Temporal Changes in Matrix Protein Synthesis and mRNA Expression During Mineralized Tissue Formation by Adult Rat Bone Marrow Cells in Culture, J. Bone Miner Res., 1994, pp. 231-240, vol. 9, No. 2.

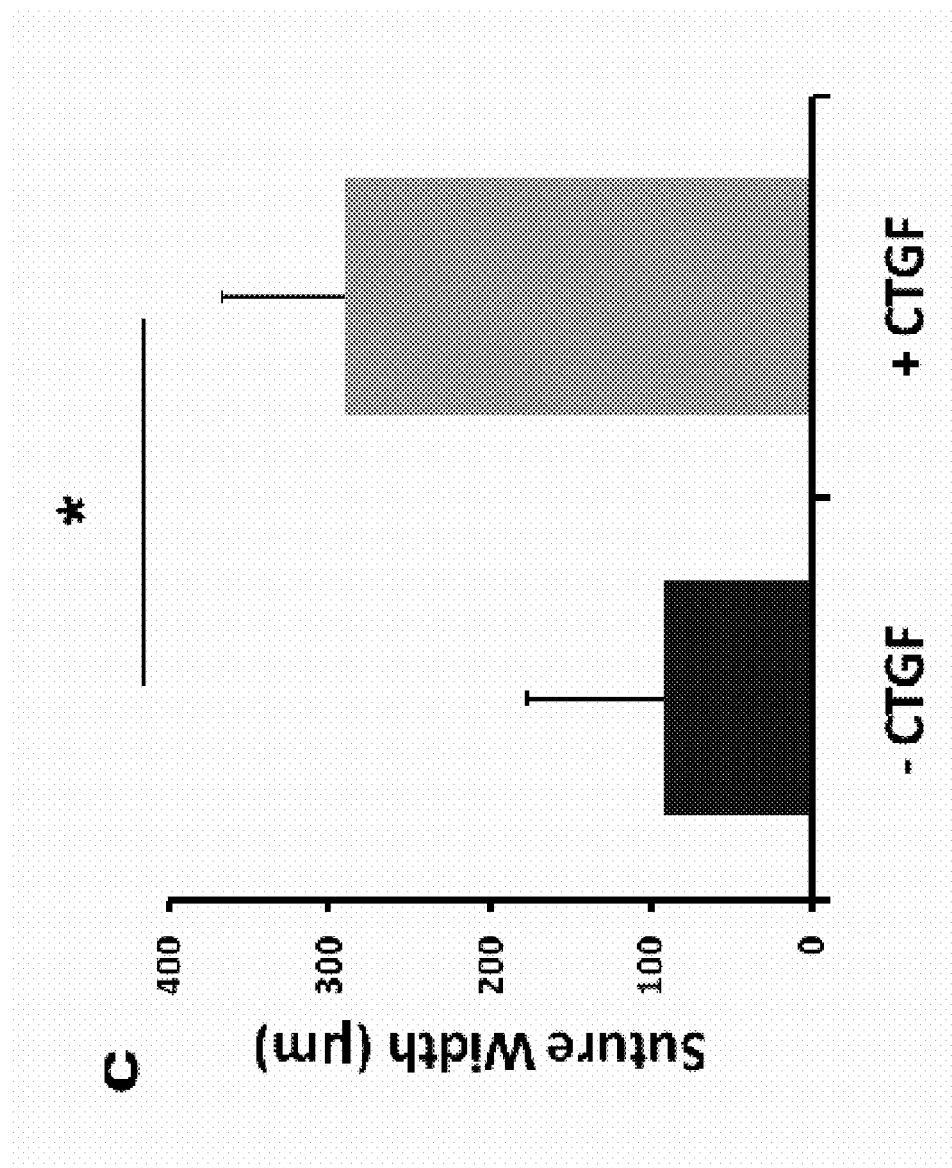

TREATMENT FOR BONE FORMATION DISORDERS BY GROWTH FACTOR DELIVERY

CROSS-REFERENCE TO RELATED APPLICATIONS

The present application is a Continuation of U.S. Nonprovisional application Ser. No. 12/439,669 filed 14 Oct. 2009, which is a Continuation-in-Part of International Application No. PCT/US2007/018667 filed 22 Aug. 2007, which claims the benefit of priority to U.S. Provisional Application Ser. No. 60/824,070 filed 30 Aug. 2006; each of which is hereby incorporated by reference in its entirety.

STATEMENT REGARDING FEDERALLY SPONSORED RESEARCH OR DEVELOPMENT

This invention was made in part with Government support under National Institutes of Health Grant Nos. R01DE15291, R01DE13964, and R01EB02332. The Government has certain rights in the invention.

INCORPORATION-BY-REFERENCE OF MATERIAL SUBMITTED IN COMPUTER READABLE FORM

The Sequence Listing, which is a part of the present disclosure, includes a computer readable form and a written sequence listing comprising nucleotide and/or amino acid sequences of the present invention. The sequence listing information recorded in computer readable form is identical to the written sequence listing. The subject matter of the Sequence Listing is incorporated herein by reference in its entirety.

FIELD OF THE INVENTION

The present invention generally relates to treatment of bone development disorders or conditions.

BACKGROUND

Bone disorders or conditions, such as synostotic conditions or ectopic mineralization most often require highly invasive treatment methodologies.

Cranial suture is soft tissue interface between calvarial bones, and has two primary functions: enabling the longitudinal growth of calvarial bones and serving as relatively immobile articulations. Functionally, cranial sutures are analogous to appendicular growth plate, both of which enable longitudinal bone growth.

Craniosynostosis refers to premature ossification of cranial sutures, and occurs in approximately one of every 2,000 live human births. Children with craniosynostosis may suffer from craniofacial deformities, seizure and mental retardation. The primary treatment for craniosynostosis is surgical craniotomy, with a major goal to relieve abnormally high intracranial pressure. Craniotomy is a traumatic surgery, involving the reshaping of skull bones and removal of synostosed bone of empirical size (Mooney et al. (2004) Expert Opin Biol Ther 4, 279-299). Surgically corrected craniosynostosis may refuse, necessitating secondary surgeries.

Recent reports disclose a tissue-engineered cranial suture-like structure and the use of TGFβ3 to modulate synostosed cranial sutures (Hong and Mao (2004) J Dental Res 83, 751-756; Moioli et al. (2006) Tissue Eng 12, 537-546), consistent with the observation that TGFβ3 modulates the fate of both natural and synostosed cranial sutures (Opperman et al. (2002) Orthod Craniofacial Res 5, 5-16). TGFβ3 attenuates not only the osteogenic differentiation of bone marrow derived osteoblasts, but also osteoblastic matrix synthesis (Moioli et al., 2006). However, little is known whether other cytokines also regulate sutural morphogenesis.

Thus, there exists the need for a minimally invasive approach for treatment of bone disorders or conditions.

SUMMARY

Disclosed herein is a new approach towards minimally invasive treatment of bone formation disorders or conditions or ectopic mineralization conditions utilizing introduction of compositions comprising a connective tissue growth factor (CTGF). The therapeutic strategy described herein is based, at least in part, on the observation that the promotion of fibroblast differentiation and/or inhibition of osteoblast differentiation, via administration of certain growth factors such as CTGF, can delay the ossification of synostosing cranial sutures.

One aspect provides a method of treating a bone formation condition or disorder or ectopic mineralization condition in a subject comprising administering a composition comprising connective tissue growth factor (CTGF) to a tissue site in a subject in need thereof.

Another aspect provides a method of delaying ossification of synostosing cranial sutures comprising administering a composition comprising CTGF to a cranial suture of a subject in need thereof.

In some embodiments, the ectopic mineralization condition comprises an ectopic calcification condition selected from the group consisting of scleroderma, urethral stone, cardiac valve mineralization and atherosclerosis.

In some embodiments, the bone formation condition or disorder comprises a synostotic condition selected from the group consisting of synostitic sagittal synostosis, metopic synostosis, lambdoid synostosis, unilateral coronal synostosis, bicoronal synostosis, multiple suture synostosis, or syndromic craniosynostosis. In some configurations, the bone formation condition or disorder comprises craniosynostosis and the composition is administered to a cranial suture of a subject in need thereof. In some embodiments, the method further comprises accessing a cranial suture of the subject.

In some embodiments, administering the composition results in at least one of (i) promotion of fibroblast differentiation, (ii) inhibition of osteoblast differentiation, or (iii) promotion of fibroblast differentiation and inhibition of osteoblast differentiation.

In some embodiments, the composition further comprises at least one: of a transforming growth factor beta (TGFβ); a basic fibroblast growth factor (bFGF); a bone morphogenetic protein (BMP); a vascular endothelial growth factor (VEGF); an osteoprotegerin; and a periostin polypeptide.

In some embodiments, the composition is injected in, at, or near the tissue site of the subject. In some configurations, the composition is injected in, at, or near a cranial suture of the subject In some embodiments, the composition comprises CTGF in a concentration of at least about 0.1 ng/ml to about 100 mg/ml. In some configurations, the composition comprises CTGF in a concentration of about 50 ng/ml.

In some embodiments, the composition is administered via a carrier delivery system. In some configurations, the carrier delivery system comprises a polymeric microsphere. In some configurations, the composition is encapsulated in a polymeric microsphere. In some configurations, the composition is encapsulated in a polymeric microsphere at a ratio of about 250 mg polymer to about 10 μg of CTGF. In some configurations, administering the composition comprises introducing a collagen sponge comprising about 5 to about 15 mg of CTGF-encapsulated microspheres to a cranial suture.

In some embodiments, the composition comprises a pharmaceutically acceptable carrier or excipient. In some embodiments, the composition comprises an immunosuppressive agent. In some embodiments, the composition comprises an antibiotic. In some embodiments, the composition comprises two or three of a pharmaceutically acceptable carrier or excipient; an immunosuppressive agent; and an antibiotic.

In some embodiments, administering the composition comprises transforming a host cell to express SEQ ID NO: 1, or a polypeptide having at least about 95% sequence identity thereto and CTGF activity; introducing the transformed host cell to the tissue site; and expressing the encoded polypeptide having CTGF activity at or near the tissue site.

In some embodiments, administering the composition comprises introducing a construct comprising a polynucleotide of SEQ ID NO: 2, or a polypeptide having at least about 95% sequence identity thereto and CTGF activity, operably linked to a promoter; introducing the construct to the tissue site; and expressing the encoded polypeptide having CTGF activity at or near the tissue site.

In some embodiments, the method further comprises administering a fibroblast cell to the tissue site of the subject. In some embodiments, the method further comprises administering a progenitor cell to the tissue site of the subject and inducing progenitor cell differentiation to a fibroblast cell by contacting the progenitor cell with CTGF.

Other objects and features will be in part apparent and in part pointed out hereinafter.

BRIEF DESCRIPTION OF THE DRAWINGS

Those of skill in the art will understand that the drawings, described below, are for illustrative purposes only. The drawings are not intended to limit the scope of the present teachings in any way.

FIG. 1 is a series of micrographs showing ex vivo morphogenesis of cranial suture in organ culture. Micrographs of H&E stained sections through the native interfrontal suture by postnatal day 10 or p10 (FIG. 1A), p25 suture without CTGF delivery (FIG. 1B), and p25 suture with 50 ng/mL CTGF (FIG. 1C). b: bone; sm: suture mesenchyme; p: periosteum; dm: dura mater; scale: 60 μm.

FIG. 2 is a series of microcomputed tomography images and a pair of bar graphs. FIG. 2C shows suture width (μm) for −CTGF and +CTGF.

FIG. 4 is an SEM image, a line and scatter plot, a series of microcomputed tomography images, and a series of immunofluorescence images.

FIG. 5 is a series of immunofluorescence images.

FIG. 6D is an immunofluorescence image showing cranial suture stained for osteopontin with CTGF treatment. Light to medium grey areas correspond to osteopontin staining.

FIG. 7 is a series of images depicting trichrome staining of tissue sections. The trichrome staining shows marked collagen synthesis upon CTGF for 4 wks. exposed to 100 ng/ml recombinant human CTGF and 50 μg/ml ascorbic acid for 4 weeks (FIG. 7B) and controls (FIG. 7A).

DETAILED DESCRIPTION OF THE INVENTION

Figures 1A, 1B, 1C:
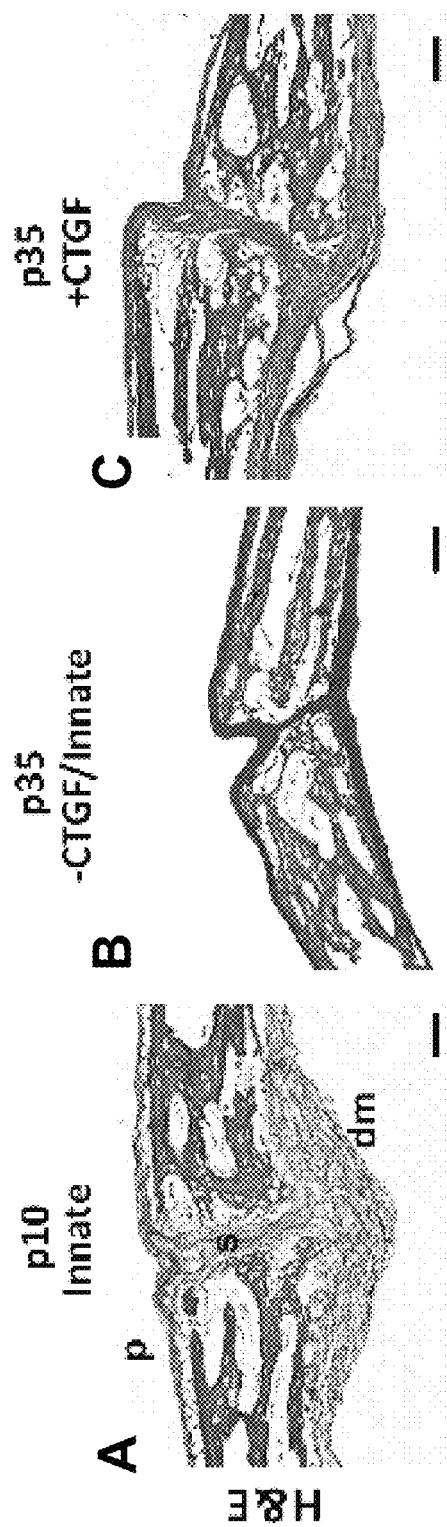
In FIG. 1A-C, uniformly darker grey areas correspond to eosinophilic structures, such as intracellular or extracellular protein or red blood cells; while mottled lighter grey areas correspond to areas having more basophilic structures, such as those containing nucleic acids, such as the ribosomes and the chromatin-rich cell nucleus, and the cytoplasmatic regions rich in RNA. Micrographs of immunohistochemistry stain for fibroblast-specific protein-1 (FSP1) through the native interfrontal suture by postnatal day 10 or p10 (FIG. 1D), p25 suture without CTGF delivery (FIG. 1E), and p25 suture with 50 ng/mL CTGF (FIG. 1F).

The approaches described herein are based at least in part upon application of the discovery that certain growth factors can delay the ossification of synostosing cranial sutures via the promotion of fibroblast differentiation and/or inhibition of osteoblast differentiation. Such observations provide for the treatment of ectopic mineralization (e.g., calcification) including scleroderma, urethral stone, cardiac valve mineralization and atherosclerosis, bone formation/developmental disorders, such as craniosynostosis, and to orchestrate ligament and tendon regeneration to bone as well as tissue engineering and regeneration of interstitial fibrous tissue, tendons, ligaments, cranial sutures, fascia, periosteum, and any internal organs with interstitial fibrous tissue. Disclosed herein is a new approach towards a minimally invasive craniofacial surgery utilizing delivery of such growth factors.

As described herein, craniosynostosis is attributed at least in part to premature ossification of cranial sutures. Conditions resultant from premature cranial suture ossification can, therefore, be treated in a subject in need thereof by administering an agent that inhibits osteogenic differentiation and/or stimulates fibroblastic differentiation. As shown herein, connective tissue growth factor (CTGF) can delay ossification of the cranial suture. Without being bound by a particular theory, it is thought that such delay in ossification of the cranial suture is due at least in part to stimulation of fibroblastic differentiation by CTGF. The ability to treat craniosynostosis with a single growth factor, for example CTGF, can provide reduced cost, increased convenience, and reduced toxicity. It is also contemplated that other growth factors can be administered with CTGF. For example, TGFβ is reported to inhibit osteogenic differentiation. Thus, growth factors such as these can be used singly, or in combination, so as to rescue premature cranial suture ossification. It is further contemplated that fibroblast cells can be administered as part of the therapeutic strategy described herein.

Described herein is an approach to modulate the homeostasis of fibrogenesis and osteogenesis by delivery of growth factors, such as connective tissue growth factor (CCN2/CTGF). Results reported herein show free-form CCN2/CTGF rescued a synostosing calvarial suture from synostosis in organ culture. Also shown was CCN2/CTGF suppressed osteocalcin expression, and stimulated fibrogenesis in calvarial suture populated with abundant cells that are positive to key fibroblast hallmarks including tenascin-C, vimentin, and FSP1. Also shown was in vivo delivery of microencapsulated CCN2/CTGF diminished osteopontin expression, and restored the morphogenesis of synostosed calvarial suture microscopically and anatomically with substantial FSP1- and vimentin-positive cells. In the experimental data provided herein, synostosis occurred ex vivo and in vivo without CCN2/CTGF delivery. Thus CCN2/CTGF has been shown to tip the balance between fibrogenesis and osteogenesis, and can be delivered preemptively or post-pathologically, or both, to treat ectopic mineralization including scleroderma, urethral stone, cardiac valve mineralization and atherosclerosis, or to orchestrate ligament and tendon regeneration to bone, or combinations thereof.

One aspect of the invention provides for a method of treating a developing bone disorder or ectopic mineralization in a subject by administering at least one tissue growth factor to the subject in need thereof.

In some embodiments, a synostotic condition (e.g., craniosynostosis) is treated by accessing a cranial suture of the subject, preferably with a minimally invasive means, and administering at least one tissue growth factor to the subject in need thereof. Such tissue growth factor(s) preferably can inhibit osteogenic differentiation and/or stimulate fibroblastic differentiation so as to delay the ossification of the cranial suture. Preferably, the growth factors are microencapsulated for controlled release and injected in or near the cranial suture. Delivery is preferably via minimally invasive means, such as through injection in, at, or near the cranial sutures of the subject.

A determination of the need for treatment will typically be assessed by a history and physical exam consistent with craniosynostosis. Examination can include, but is not limited to, physical examination and radiographic studies, including plain radiography and computed tomography (CT), clinical history including complications of pregnancy, duration of gestation, and birth weight, and history of infant sleeping position. Synostotic conditions treatable by the methods disclosed herein include, but are not limited to, sagittal synostosis, metopic synostosis, lambdoid synostosis, unilateral coronal synostosis (plagiocephaly), and bicoronal synostosis (brachycephaly), multiple suture synostosis, and syndromic craniosynostosis (e.g., Crouzon's syndrome, Apert's syndrome (acrocephalosyndactyly), Pfeiffer's disease, Saethre-Chotzen syndrome). Secondary craniosynostosis conditions, such as metabolic disorders (e.g., hyperthyroidism), malformations (e.g., holoprosencephaly, microcephaly, shunted hydrocephalus, encephalocele), exposure of fetus (e.g., valproic acid, phenytoin), and mucopolysaccharidosis (e.g., Hurler's syndrome, Morquio's syndrome), can also be treated according to the methods described herein. Diagnosis of craniosynostosis is within the skill of the art. Subjects with an identified need of therapy include those with a diagnosed condition described herein or indication of a condition amenable to therapeutic treatment described herein and subjects who have been treated, are being treated, or will be treated for such conditions. The subject is preferably an animal, including, but not limited to, mammals, reptiles, and avians, more preferably horses, cows, dogs, cats, sheep, pigs, and chickens, and most preferably human.

In some embodiments, an ectopic mineralization condition or disorder, such as ectopic calcification, is treated by accessing a tissue site of the subject, preferably with a minimally invasive means, and administering at least one tissue growth factor to the subject in need thereof. Ectopic calcification is generally understood to be inappropriate biomineralization occurring in soft tissues (see e.g., Giachelli (1999) American Journal of Pathology 154, 671-675). Ectopic calcifications can comprise calcium phosphate salts (e.g., hydroxyapatite) and calcium oxalates and octacalcium phosphate. Ectopic mineralization can occur in most soft tissues, including but not limited to skin, breast, ovaries, uterus, kidney, tendons, and cardiovascular tissues, as well as in or around a prosthetic device. Diagnosis of an ectopic mineralization condition is within the skill of the art. In some embodiments, the treated ectopic mineralization condition comprises at least one of scleroderma, urethral stone, cardiac valve mineralization, and atherosclerosis.

Growth Factors

According to the methods described herein, growth factors capable of inhibiting osteogenic differentiation and/or stimulating fibroblastic differentiation are administered to a subject in need thereof. One such growth factor is connective tissue growth factor (CTGF), which, as shown below, delays ossification of the cranial suture. CTGFs are a class of proteins thought to have growth-promoting activities on connective tissues. Known members of the CTGF family include, but are not limited to, CTGF-1, CTGF-2, and CTGF-4. Preferably, the CTGF is human CTGF or recombinant human CTGF. Various CTGFs are commercially available (e.g., BioVendor, Chandler, N.C.).

In some embodiments, CTGF administered to a subject comprises the polypeptide of SEQ ID NO: 1, or a polypeptide comprising a sequence having at least about 85% sequence identity thereto and CTGF activity. For example, the CTGF can comprise a polypeptide comprising a sequence having at least about 90%, at least about 95%, or at least about 99% sequence identity to SEQ ID NO: 1 and CTGF activity.

Nucleotide and/or amino acid sequence identity percent (%) is understood as the percentage of nucleotide or amino acid residues that are identical with nucleotide or amino acid residues in a candidate sequence in comparison to a reference sequence when the two sequences are aligned. To determine percent identity, sequences are aligned and if necessary, gaps are introduced to achieve the maximum percent sequence identity. Sequence alignment procedures to determine percent identity are well known to those of skill in the art. Often publicly available computer software such as BLAST, BLAST2, ALIGN2 or Megalign (DNASTAR) software is used to align sequences. Those skilled in the art can determine appropriate parameters for measuring alignment, including any algorithms needed to achieve maximal alignment over the full-length of the sequences being compared. When sequences are aligned, the percent sequence identity of a given sequence A to, with, or against a given sequence B (which can alternatively be phrased as a given sequence A that has or comprises a certain percent sequence identity to, with, or against a given sequence B) can be calculated as: percent sequence identity=X/Y100, where X is the number of residues scored as identical matches by the sequence alignment program's or algorithm's alignment of A and B and Y is the total number of residues in B. If the length of sequence A is not equal to the length of sequence B, the percent sequence identity of A to B will not equal the percent sequence identity of B to A.

CTGF can be administered in conjunction with other growth factors. Other growth factors that can be co-administered with CTGF include, but are not limited to Transforming Growth Factor beta (TGFβ) and basic fibroblast growth factor (e.g., bFGF or FGF2). TGFβs are a class of proteins thought to have growth-promoting activities on a range of tissues, including connective tissues. Known members of the TGFβ family include, but are not limited to, TGFβ-1, TGFβ-2, and TGFβ-3. Preferably, the TGFβ is human TGFβ or recombinant human TGFβ. Various TGFβs, including TGFβ3, are commercially available (e.g., BioVision, Inc., Mountain View, Calif.). As an example, CTGF and TGFβ3 (reported to inhibit osteogenic differentiation, see Moioli et al., 2006) can be administered together or sequentially to the subject to delay ossification of the cranial suture. Other growth factors that can be administered include Bone Morphogenetic Protein (BMP), Vascular Endothelial Growth Factor (VEGF), Osteoprotegerin, and Periostin polypeptides.

Growth factors described above can be administered in formulations as, for example, isolated polypeptides or polynucleotides. Polynucleotide compositions of the growth factors include, but are not limited to, gene therapy vectors harboring polynucleotides encoding the growth factor polypeptides of interest. Gene therapy methods require a polynucleotide that codes for the growth factor polypeptide operatively linked or associated to a promoter and any other genetic elements necessary for the expression of the growth factor polypeptide by the target tissue. Such gene therapy and delivery techniques are known in the art (see e.g., Smyth Templeton (2003) Gene and Cell Therapy, CRC, ISBN 0824741048). Suitable gene therapy vectors include, but are not limited to, gene therapy vectors that do not integrate into the host genome. Alternatively, suitable gene therapy vectors include, but are not limited to, gene therapy vectors that integrate into the host genome.

A polynucleotide of the invention can be delivered in plasmid formulations. Plasmid DNA or RNA formulations generally include sequences encoding growth factor polypeptides that are free from any delivery vehicle that acts to assist, promote or facilitate entry into the cell, including viral sequences, viral particles, liposome formulations, lipofectin or precipitating agents and the like. Optionally, gene therapy compositions of the embodiments can be delivered in liposome formulations and lipofectin formulations, which can be prepared by methods well known to those skilled in the art (see e.g., Smyth Templeton (2003) Gene and Cell Therapy, CRC, ISBN 0824741048). Gene therapy vectors can further comprise suitable adenoviral vectors including, but not limited to for example, those described in Curiel and Douglas (2002) Adenoviral Vectors for Gene Therapy, Academic Press, ISBN 0121995046.

Any of the transcribable polynucleotide molecule sequences described above can be provided in a construct. Constructs of the present invention generally include a promoter functional in a host cell operably linked to a transcribable polynucleotide molecule for a growth factor, such as provided in SEQ ID NO: 1, and variants thereof as discussed above. Promoter selection can allow expression of a desired gene product, such as CTGF, under a variety of conditions. Promoters can also be selected on the basis of their regulatory features. Examples of such features include enhancement of transcriptional activity and inducibility. The promoter can be an inducible promoter. For example, the promoter can be induced according to temperature, pH, a hormone, a metabolite (e.g., lactose, mannitol, an amino acid), light (e.g., wavelength specific), osmotic potential (e.g., salt induced), a heavy metal, or an antibiotic. Numerous standard inducible promoters will be known to one of skill in the art.

The term "construct" is understood to refer to any recombinant polynucleotide molecule such as a plasmid, cosmid, virus, autonomously replicating polynucleotide molecule, phage, or linear or circular single-stranded or double-stranded DNA or RNA polynucleotide molecule, derived from any source, capable of genomic integration or autonomous replication, comprising a polynucleotide molecule where one or more polynucleotide molecule has been linked in a functionally operative manner, i.e. operably linked. The term "vector" or "vector construct" is understood to refer to any recombinant polynucleotide construct that may be used for the purpose of transformation, i.e., the introduction of heterologous DNA into a host cell.

A growth factor polypeptide, such as CTGF, can be delivered to a subject by transforming a host cell to express the polypeptide and introducing the transformed cell into the subject. Host cells can be transformed using a variety of standard techniques known to the art (see, e.g., Sambrook and Russel (2006) Condensed Protocols from Molecular Cloning: A Laboratory Manual, Cold Spring Harbor Laboratory Press, ISBN-10: 0879697717; Ausubel et al. (2002) Short Protocols in Molecular Biology, 5th ed., Current Protocols, ISBN-10: 0471250929; Sambrook and Russel (2001) Molecular Cloning: A Laboratory Manual, 3d ed., Cold Spring Harbor Laboratory Press, ISBN-10: 0879695773; Elhai, J. and Wolk, C. P. 1988. Methods in Enzymology 167, 747-754). Such techniques include, but are not limited to, viral infection, calcium phosphate transfection, liposome-mediated transfection, microprojectile-mediated delivery, receptor-mediated uptake, cell fusion, electroporation, and the like. The transfected cells can be selected and propagated to provide recombinant host cells that comprise the expression vector stably integrated in the host cell genome.

Polypeptide compositions of the isolated osteoinductive agents include, but are not limited to, CTGF and TGFβ polypeptides. Polypeptide compositions of the osteoinductive agents include, but are not limited to, isolated full-length proteins, fragments and variants thereof. Preferably, polypeptide fragments of the osteoinductive agents comprise, or alternatively consist of, propeptide forms of the isolated full-length polypeptides. Polypeptide fragments of the growth factor agents can comprise, or alternatively consist of, mature forms of the isolated full-length polypeptides. Also preferred are the polynucleotides encoding the propeptide and mature polypeptides of the growth factor agents.

Variants of the growth factor agents include, but are not limited to, protein variants that are designed to increase the duration of activity of the growth factor agent in vivo. For example, a variant osteoinductive agent includes full length proteins or fragments thereof that are conjugated to polyethylene glycol (PEG) moieties to increase their half-life in vivo (also known as pegylation).

The growth factor agent(s) can be provided in formulation(s) as fusion proteins. For example, the growth factor agent(s) can be fusion proteins with the $F_c$ portion of human IgG. As another example, the growth factor agent(s) can be hetero- or homodimers or multimers. Examples of preferred fusion proteins include, but are not limited to, ligand fusions between mature growth factor polypeptides and the $F_c$ portion of human Immunoglobulin G (IgG). Methods of making fusion proteins and constructs encoding the same are well known in the art.

Various embodiments further contemplate the use of polynucleotides and polypeptides, which can inhibit osteogenic differentiation and/or stimulate fibroblastic differentiation, having at least 80% sequence identity to the isolated polynucleotides and polypeptides of the growth factors described herein. For example, polynucleotides and polypeptides can have at least 81%, 82%, 83%, 84%, 85%, 86%, 87%, 88%, 89%, 90%, 91%, 92%, 93%, 94%, 95%, 96%, 97%, 98%, or 99% sequence identity to the isolated polynucleotides and polypeptides of the growth factors described herein.

Growth factors can be administered at concentrations of from about 0.1 ng/ml to about 100 mg/ml. For example, growth factors can be administered at concentrations of about 0.1 ng/ml, 1 ng/ml, 10 ng/ml, 100 ng/ml, 1 mg/ml, 10 mg/ml, or 100 mg/ml. As another example, a growth factor can be administered at concentrations of about 50, 100, 150, 200, 250, 300, 350, 400, 450, 500, 550, 600, 700, 750, 800, 850, 900, 950, or 1000 ng/mL. As a further example, CTGF can be administered at about 50 ng/ml. Growth factors can be administered at a pH of about 3 to 8.

Growth factor agents and/or growth factor formulations preferably are sterile. For example, sterility can be readily accomplished by filtration through sterile filtration membranes (e.g., 0.2 micron membranes or filters).

As one of skill in the art will recognize, the concentrations of CTGF, or other growth factor agents, can be variable based on the desired length or degree of attenuation of sutural ossification. Similarly, one of skill in the art will understand that the duration of sustained release can be modified by the manipulation of the compositions comprising the sustained release formulation, such as for example, modifying the percent of biostable polymers found within a sustained release polymer.

Fibroblast Cells

Fibroblast cells can be administered in conjunction with the growth factors capable of attenuating ossification. As described above, the therapeutic strategy herein is based at least in part on inhibiting osteogenic differentiation and/or stimulating fibroblastic differentiation so as to attenuate ossification of synostosing cranial sutures. Pursuant to such, administration of exogenous fibroblast cells in conjunction with the growth factors described herein can further attenuate ossification of synostosing cranial sutures. Preferably, the fibroblast cells are obtained from the same subject to which they are administered. Isolation, culture, and administration of fibroblast cells are generally known in the art (see e.g., Vunjak-Novakovic and Freshney (2006) Culture of Cells for Tissue Engineering, Wiley-Liss, ISBN 0471629359).

In some embodiments, fibroblast cells are differentiated from progenitor cells, such as human mesenchymal cells (hMSCs). Differentiation of fibroblast cells can occur ex vivo, prior to introduction to a treated tissue site, or in vivo after introduction to a treated tissue site.

Progenitor cells can be differentiated into fibroblasts using chemical factors, such as by the treatment of CTGF and ascorbic acid. As demonstrated herein, monolayer-cultured hMSCs treated with CTGF cocktail showed significant increases in markers for fibroblastic differentiation (see e.g., Example 17). The inducement of ex vivo differentiation of hMSCs into fibroblasts, as described herein, can be applied to tissue engineering and tissue regeneration of interstitial fibrous tissue, tendons, ligaments, cranial sutures, fascia, periosteum, and any internal organs with interstitial fibrous tissue.

Provided herein is an ex vivo culturing protocol for fibroblastic differentiation of tissue progenitor cells (e.g., hMSCs) using bioactive factors such as connective tissue growth factor (CTGF). As demonstrated herein, the treatment with recombinant human CTGF on cultured hMSCs showed significant increases in type I collagen and tenascin-C (Tn-C) contents by 2 and 4 wks (see e.g., Example 17). In addition, CTGF-treated hMSCs failed to show osteogenic or chondrogenic differentiation (see e.g., Example 18). Thus is demonstrated that CTGF is an effective induction factor for fibroblastic differentiation of hMSCs.

Generally, the tissue progenitor cell is a precursor to tissue of interest and differentiates in the presence of CTGF. Such cells can be isolated, purified, and/or cultured by a variety of means known to the art Methods for the isolation and culture of tissue progenitor cells are discussed in, for example, Vunjak-Novakovic and Freshney (2006) Culture of Cells for Tissue Engineering, Wiley-Liss, ISBN 0471629359. The tissue progenitor cells can be derived from the same or different species as the transplant recipient. For example, the progenitor cells can be derived from an animal, including, but not limited to, mammals, reptiles, and avians, more preferably horses, cows, dogs, cats, sheep, pigs, and chickens, and most preferably human.

Connective tissue growth factor is available from a variety of commercial sources (e.g., BioVendor Laboratory Medicine, Inc., Candler, N.C.). Preferably, the connective tissue growth factor is preferably human connective tissue growth factor (e.g., Accession No. NP_001892). Connective tissue growth factor for differentiating tissue progenitor cells to fibroblasts can be supplied at, for example, a concentration of about 0 to 1000 ng/mL. For example, the growth factor can be present at a concentration of about 50, 100, 150, 200, 250, 300, 350, 400, 450, 500, 550, 600, 700, 750, 800, 850, 900, 950, or 1000 ng/mL.

The fibroblast progenitor cell contacted with the connective tissue growth factor can be incubated under conditions allowing differentiation to a fibroblast cell. Methods of culturing progenitor cells are generally known in the art and such methods can be adapted so as to provide optimal conditions for differentiation of progenitor cells contacted with connective tissue growth factor.

Carriers

The growth factor formulations containing growth factors capable of attenuating ossification (e.g., CTGF) can be made available as immediate release formulations, sustained release formulations, or both. One of skill in the art could determine whether a subject would benefit from immediate release formulations or sustained release formulations based on factors such as age and level of physical activity.

Immediate release formulations include liquid formulations comprising at least CTGF applied to target area. The liquid formulations provide the growth factors in bioavailable form at rates dictated by the fluid properties of the liquid formulation, such as diffusion rates at the site of implantation, the influence of endogenous fluids, etc. Examples of suitable liquid formulations comprise water, saline, or other acceptable fluid mediums that will not induce host immune responses. Skilled artisans recognize that the growth factors need to reside at the situs of defect long enough to attenuate sutural ossification, and preferably should not seep to surrounding areas where normal bone growth is desired. Using the guidelines provided herein, those skilled in the art are capable of designing a suitable formulation for delivery.

The growth factors capable of attenuating ossification (e.g., CTGF) can be can be encapsulated and administered in a variety of carrier delivery systems. The carrier material can contain, be coated with, or infused with such growth factors. Examples of carrier materials that can be used in such fashion include, but are not limited to, polymeric delivery systems (e.g., biodegradable polymer material, collagen sponge), granules of an appropriate material (e.g., demineralized bone granules, calcium phosphate-containing granules, etc.), and bone putty. The carrier material can also contain allograft, DBM (demineralized bone matrix) calcium phosphates (e.g., hydroxyapatites, and tricalcium phosphates), calcium sulphates, sulphate salts, autograft, and the like, as well as mixtures or combinations of these.

Controlled release formulations contain growth factors capable of attenuating ossification (e.g., CTGF) along with a carrier delivery system. The duration of release from the sustained release formulations is dictated by the nature of the formulation and other factors, such as for example, proximity to bodily fluids, as well as density of application of the formulations, degradation rates of biodegradeable polymers comprising the growth factor formulations, and other factors. However, sustained release formulations can be designed to provide CTGF (and/or other growth factors) in the formulations at relatively consistent concentrations in bioavailable form over extended periods of time.

The carrier delivery system generally encapsulates the biomolecule of interest and provides controlled release of the agent over extended periods of time. Generally a carrier includes molecules conjugated to, mixed with, or used for encapsulating growth factors capable of attenuating ossification (e.g., CTGF). Carrier-based systems for biomolecular agent delivery can: tailor biomolecule/agent release rates; increase the proportion of biomolecule that reaches its site of action; improve the transport of the drug to its site of action; allow colocalized deposition with other agents or excipients; improve the stability of the agent in vivo; prolong the residence time of the agent at its site of action by reducing clearance; decrease the nonspecific delivery of the agent to nontarget tissues; decrease irritation caused by the agent; decrease toxicity due to high initial doses of the agent; alter the immunogenicity of the agent; decrease dosage frequency, improve taste of the product; and/or improve shelf life of the product.

Polymeric release systems can be used to deliver growth factors capable of attenuating ossification (e.g., CTGF) (see Whittlesey and Shea (2004) Experimental Neurology 190, 1-16). Polymeric systems can also be designed to deliver multiple biomolecules that can act synergistically or sequentially on cellular processes. Polymeric delivery systems can maintain therapeutic levels of growth factors, such as CTGF, described herein, reduce harmful side effects, decrease the amount of biomolecule required, decrease the number of dosages, and facilitate delivery of agents with short in vivo half-lives. Release rates can be controlled by altering the pore size, structure, and polymer contents of synthetic polymers such as the nondegradable synthetic polymer EVAc and the degradable synthetic polymer polyester PLGA. Furthermore, the degradation of the material itself serves to govern release profiles, providing an additional level of control over release rate. Polymeric delivery systems described herein can be tailored for release durations of, for example, minutes, hours, days, weeks, and even years depending upon the physical and chemical properties of the delivered molecule, the polymer employed, and the processing conditions used during fabrication.

Both natural (e.g., collagen) and synthetic polymers (e.g., silicone, poly-lactide-co-glycolide (PLGA), and polyethylene vinyl-co-acetate (EVAc)) can be utilized for the local delivery of growth factors capable of attenuating ossification (e.g., CTGF). Biodegradable polymers are preferable for biomolecule delivery because the device can disappear over time, eliminating the need for surgical retrieval. PLGA is a widely used biopolymer due to its commercial availability, controllable degradation rate, proven biocompatibility, and FDA approval (see e.g., Lu et al. (2000) Biomaterials 21, 1837-1845). Polyanhydrides are a similar class of degradeable polymer that can be used for biomolecule delivery.

Polymeric microspheres can facilitate delivery of growth factors, such as CTGF and/or TGFβ, described herein. For example, sustained delivery microspheres can be stereotactically injected to release a polypeptide or polynucleotide of the growth factor at a target site (e.g., a cranial suture). Microspheres are produced using naturally occurring or synthetic polymers to produce particulate systems in the size range of 0.1 to 500 μm. Generally, microspheres are physically and chemically more stable than liposomes and allow for higher agent loading. Polymeric micelles and polymeromes are polymeric delivery vehicles with similar characteristics to microspheres and can also facilitate encapsulation and delivery of growth factors, such as CTGF and/or TGFβ, described herein. Fabrication, encapsulation, and stabilization of microspheres for biomolecular payloads such as growth factors are within the skill of the art (see e.g., Varde & Pack (2004) Expert Opin. Biol. 4(1)35-51). Polymer materials useful for forming microspheres include PLA, PLGA, PLGA coated with DPPC, DPPC, DSPC, EVAc, gelatin, albumin, chitosan, dextran, DL-PLG, SDLMs, PEG (e.g., ProMaxx), sodium hyaluronate, diketopiperazine derivatives (e.g., Technosphere), calcium phosphate-PEG particles, and oligosaccharide derivative DPPG (e.g., Solidose). Encapsulation can be accomplished, for example, using a water/oil single emulsion method, a water-oil-water double emulsion method, or lyophilization. Several commercial encapsulation technologies are available (e.g., ProLease®, Alkerme). Release rate of microspheres can be tailored by type of polymer, polymer molecular weight, copolymer composition, excipients added to the microsphere formulation, and microsphere size.

Polymeric hydrogels, composed of hydrophillic polymers such as collagen, fibrin, and alginate, can also be used for the sustained release of incorporated growth factors, such as CTGF and/or TGFβ (see e.g., Sakiyama et al. (2001) FASEB J. 15, 1300-1302). Biomolecules incorporated into the hydrogel can stimulate cellular function directly from the matrix or following release.

Three-dimensional polymeric implants, on the millimeter to centimeter scale, can be loaded with growth factors, such as CTGF and/or TGFβ (see e.g., Teng et al (2002) Proc. Natl. Acad. Sci. U.S.A. 99, 3024-3029). These polymeric implants can serve a structural function for cell adhesion while also providing controlled release of biomolecules. A polymeric implant typically provides a larger depot of the bioactive factor. The implants can also be fabricated into structural supports, tailoring the geometry (e.g., shape, size, porosity) to the application (e.g., conforming to the cranial suture). Three-dimensional polymeric implants for biomolecule delivery can be formulated in a variety of means known to the art including, but not limited to, emulsion methods, solvent casting, and carbon dioxide foaming process (see e.g., Whittlesey and Shea (2004) Experimental Neurology 190, 1-16). Implantable matrix-based delivery systems are also commercially available in a variety of sizes and delivery profiles (e.g., Innovative Research of America, Sarasota, Fla.).

As an alternative to release, biomolecules can be immobilized on or in polymeric delivery systems. This approach includes substrate mediated delivery and solid-phase delivery. Generally, the polymeric substrate functions to support cell adhesion and place the biomolecular cargo directly in the cellular microenvironment (see e.g., Whittlesey and Shea (2004) Experimental Neurology 190, 1-16). Substrate mediated delivery can be used to deliver both nonviral and viral vectors. This approach is especially preferable for viral vector delivery as it mimics how many such vectors associate with the extracellular matrix as a means to facilitate cellular binding and internalization. For example, implantation of an adenovirus-modified collagen gel can result in transduction throughout the matrix with a differing delivery profile as compared to direct injection, thus localizing gene delivery and avoiding distal side effects (see e.g., Levy et al. (2001) Gene Ther. 8, 659-667).

Liposome can be used to facilitate the delivery of growth factors, such as CTGF and/or TGFβ, to the target site. The drug carrying capacity and release rate of liposomes can depend on the lipid composition, size, charge, drug/lipid ratio, and method of delivery. Conventional liposomes are composed of neutral or anionic lipids (natural or synthetic). Commonly used lipids are lecithins such as (phosphatidylcholines), phosphatidylethanolamines (PE), sphingomyelins, phosphatidylserines, phosphatidylglycerols (PG), and phosphatidylinositols (PI). A commonly used method of encapsulation is rehydration of a lipid film with a biomolecule solution followed by freeze-thawing and extrusion. Other techniques for forming biomolecule liposomes include the proliposome technique (see e.g., Galovic et al. (2002) Eur. J.

Pharm. Sci. 15, 441-448) and the crossflow injection technique (see e.g., Wagner et al. (2002) J. Liposome Res. 12, 259-270). Liposome encapsulation efficiency can be monitored and optimized through various procedures known to the art, including differential scanning calorimetry (see e.g., Lo et al. (199%) J. Pharm. Sci. 84, 805-814).

Excipients can be added to the delivery system to stabilize the emulsion during fabrication and to stabilize the growth factors during fabrication and/or release. In the case of encapsulated proteins such as CTGF and/or TGFβ, addition of excipients, such as PEG, carbohydrates, and buffering salts (e.g., magnesium hydroxide), can prevent aggregation and stabilize the folded protein structure. As another example, encapsulated protein biomolecules in PLGA microspheres in the presence of the hydrophilic excipient mannitol can enhance biomolecular stability. Excipients can also impact release rate. For example, PVA in the biomolecule solution can stabilize the primary emulsion and provide more uniform distribution throughout the matrix, prevent coalescence of inner aqueous-phase droplets, and decrease initial release burst and overall release rate. Coating of microspheres can be used to alter in vivo properties. For example, coating PLGA microspheres with DPPC can decrease uptake of the biomolecule cargo into macrophages. As another example, coating particles with mucoadhesive polymers such as chitosan and hydroxypropylcellulose can increase residency time of carriers adhering to bone.

Liquid compositions that are useful for the delivery of growth factor formulations in vivo include conjugates of CTGF and/or TGFβ with a water-insoluble biocompatible polymer, with the dissolution of the resultant polymer-active agent conjugate in a biocompatible solvent to form a liquid polymer system. In addition, the liquid polymer system may also include a water-insoluble biocompatible polymer that is not conjugated to CTGF and/or TGFβ. In one embodiment, these liquid compositions may be introduced into the body of a subject in liquid form. The liquid composition then solidifies or coagulates in situ to form a controlled release implant where the growth factors are conjugated to the solid matrix polymer.

In one embodiment, the carrier material is provided without growth factor formulations incorporated within the carrier material. In this embodiment, the growth factor formulations are introduced into the carrier material prior to implantation of the material in a subject. In such a situation, CTGF and/or TGFβ agents are placed into a container having a sterile access port, for example, an intravenous solution bag or vial having a stopper pierceable by a hypodermic injection needle. In one embodiment, CTGF and/or TGFβ agents and prepared formulations are stored in separate containers, for example, sealed ampoules or vials, as an aqueous solution or as a lyophilized formulation for reconstitution. As an example of a lyophilized formulation, 10-ml vials are filled with 5 ml of sterile-filtered 1% (w/v) aqueous CTGF and/or TGFβ solution, and the resulting mixture is lyophilized. The osteoinductive agent is prepared by reconstituting the lyophilized agent prior to administration in an appropriate solution, admixed with the prepared growth factor formulations and administered to the surface of the carrier material or infused into the carrier material prior to or concurrent with implantation into a subject. Application may be achieved by, for example, immersion of the carrier material in growth factor formulations, by spraying growth factor formulations on the surface of the carrier material, or by any other means of application.

Formulations

The agents described herein can be formulated by any conventional manner using one or more pharmaceutically acceptable carriers and/or excipients as described in, for example, Remington's Pharmaceutical Sciences (A. R. Gennaro, Ed.), 21st edition, ISBN: 0781746736 (2005), incorporated herein by reference in its entirety. Such formulations will contain a therapeutically effective amount of the agent, preferably in purified form, together with a suitable amount of carrier so as to provide the form for proper administration to the subject. The formulation should suit the mode of administration.

Growth factor formulations can optionally include antibiotics that may be co-administered so as to prevent infection by obligate or opportunistic pathogens that are introduced to the subject during surgery. Antibiotics useful with the growth factor formulations include, but are not limited to, amoxicillin, beta-lactamases, aminoglycosides, beta-lactam (glycopeptide), clindamycin, chloramphenicol, cephalosporins, ciprofloxacin, erythromycin, fluoroquinolones, macrolides, metronidazole, penicillins, quinolones, rapamycin, rifampin, streptomycin, sulfonamide, tetracyclines, trimethoprim, trimethoprimsulfamthoxazole, and vancomycin.

The growth factor formulations can optionally further include immunosuppressive agents. Suitable immunosuppressive agents that may be administered in combination with the growth factor formulations of the invention include, but are not limited to, steroids, cyclosporine, cyclosporine analogs, cyclophosphamide, methylprednisone, prednisone, azathioprine, FK-506, 15-deoxyspergualin, and other immunosuppressive agents that act by suppressing the function of responding T cells. Other immunosuppressive agents that may be administered in combination with the growth factor formulations include, but are not limited to, prednisolone, methotrexate, thalidomide, methoxsalen, rapamycin, leflunomide, mizoribine (Bredinin™), brequinar, deoxyspergualin, and azaspirane (SKF 105685), Orthoclone OKT™ 3 (muromonab-CD3). Sandimmune™, Neoral™ Sangdya™ (cyclosporine), Prograf™ (FK506, tacrolimus), Cellcept™ (mycophenolate motefil, of which the active metabolite is mycophenolic acid), Imuran™ (azathioprine), glucocorticosteroids, adrenocortical steroids such as Deltasone™ (prednisone) and Hydeltrasol™ (prednisolone), Folex™ and Mexate™ (methotrxate), Oxsoralen-Ultra™ (methoxsalen) and Rapamuen™ (sirolimus).

Growth factor formulations can optionally further include a carrier vehicle such as water, saline, Ringer's solution, calcium phosphate based carriers, or dextrose solution. Nonaqueous vehicles such as fixed oils and ethyl oleate are also useful herein, as well as liposomes.

Some growth factor formulations further optionally include substances that enhance isotonicity and chemical stability. Such materials are non-toxic to subjects at the dosages and concentrations employed, and include buffers such as phosphate, citrate, succinate, acetic acid, and other organic acids or their salts; antioxidants such as ascorbic acid; low molecular weight (less than about ten residues) polypeptides, e.g., polyarginine or tripeptides; proteins, such as serum albumin, gelatin, or immunoglobulins; amino acids, such as glycine, glutamic acid, aspartic acid, or arginine; monosaccharides, disaccharides, and other carbohydrates including cellulose or its derivatives, glucose, mannose, or dextrins; chelating agents such as EDTA; sugar alcohols such as mannitol or sorbitol; counterions such as sodium; and/or nonionic surfactants such as polysorbates, poloxamers, or PEG.

Delivery

Agents for use in the methods described herein can be delivered in a variety of means known to the art. The agents can be used therapeutically either as exogenous materials or as endogenous materials. Exogenous agents are those produced or manufactured outside of the body and administered to the body. Endogenous agents are those produced or manufactured inside the body by some type of device (biologic or other) for delivery within or to other organs in the body.

The methods described herein involve delivering polypeptide growth factors (or polynucleotides encoding such growth factors), such as CTGF and/TGFβ, to developing bone sites, such as cranial sutures of a subject suffering from craniosynostosis, so as to delay ossification. Methods and apparatus for accessing the cranial suture so as to deliver agents and/or formulations described herein are within the skill of the art. Preferably, accessing the cranial suture is performed in a minimally invasive manner. However, the invention is not limited to minimally invasive methods. The invention may make use of any suitable method of accessing the bone defect including traditional, more invasive methods known to one of skill in the art. It is also contemplated that the methods described herein can be performed in conjunction with conventional surgical techniques for the treatment of craniosynostosis.

The compositions of the invention can be administered through a variety of routes well known in the arts. Examples include methods involving direct injection (e.g., stereotactic), implantation of cells engineered to secrete the growth factors of interest, drug-releasing biomaterials, implantable matrix devices, implantable pumps, injectable gels and hydrogels, liposomes, micelles (e.g., up to 30 μm), nanospheres (e.g., less than 1 μm), microspheres (e.g., 1-100 μm), reservoir devices, etc. The growth factors can be delivered to the subject by way of injection using, for example, a graft syringe.

When used in the methods of the invention, a therapeutically effective amount of one of the agents described herein can be employed in pure form or, where such forms exist, in pharmaceutically acceptable salt form and with or without a pharmaceutically acceptable excipient. For example, the agents of the invention can be administered, at a reasonable benefit/risk ratio applicable to any medical treatment, in a sufficient amount sufficient to inhibit and/or relieve symptoms associated with craniosynostosis. Administration of an effective amount of an agent will generally inhibit osteogenic differentiation and/or stimulate fibroblastic differentiation so as to delay the ossification of the cranial suture.

Toxicity and therapeutic efficacy of such agents can be determined by standard pharmaceutical procedures in cell cultures and/or experimental animals for determining the $LD_{50}$ (the dose lethal to 50% of the population) and the $ED_{50}$, (the dose therapeutically effective in 50% of the population). The dose ratio between toxic and therapeutic effects is the therapeutic index that can be expressed as the ratio $LD_{50}/ED_{50}$, where large therapeutic indices are preferred.

The amount of an agent that may be combined with a pharmaceutically acceptable carrier to produce a single dosage form will vary depending upon the host treated and the particular mode of administration. It will be appreciated by those skilled in the art that the unit content of agent contained in an individual dose of each dosage form need not in itself constitute a therapeutically effective amount, as the necessary therapeutically effective amount could be reached by administration of a number of individual doses. Agent administration can occur as a single event or over a time course of treatment. For example, an agent can be administered daily, weekly, bi-weekly, or monthly. It is contemplated that the craniosynostosis treatment described herein could extend from several weeks to several months or even a year or more.

The specific therapeutically effective dose level for any particular subject will depend upon a variety of factors including the condition being treated and the severity of the condition; activity of the specific agent employed; the specific composition employed; the age, body weight, general health, sex and diet of the patient; the time of administration; the route of administration; the rate of excretion of the specific agent employed; the duration of the treatment; drugs used in combination or coincidental with the specific agent employed and like factors well known in the medical arts. It will be understood by a skilled practitioner that the total daily usage of the agents for use in the present invention will be decided by the attending physician within the scope of sound medical judgment.

Agents that inhibit osteogenic differentiation and/or stimulate fibroblastic differentiation so as to delay the ossification of the cranial suture can also be used in combination with other therapeutic modalities. Thus, in addition to the therapies described herein, one may also provide to the subject other therapies known to be efficacious for particular conditions linked to craniosynostosis.

In some embodiments, the numbers expressing quantities of ingredients, properties such as molecular weight, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention can contain certain errors necessarily resulting from the standard deviation found in their respective testing measurements.

In some embodiments, the terms "a" and "an" and "the" and similar references used in the context of describing a particular embodiment of the invention (especially in the context of certain of the following claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience or patentability. When any such inclusion or deletion occurs, the specification is herein deemed to contain the group as modified thus fulfilling the written description of all Markush groups used in the appended claims.

Having described the invention in detail, it will be apparent that modifications, variations, and equivalent embodiments are possible without departing the scope of the invention defined in the appended claims. Furthermore, it should be appreciated that all examples in the present disclosure are provided as non-limiting examples.

EXAMPLES

The following non-limiting examples are provided to further illustrate the present invention. It should be appreciated by those of skill in the art that the techniques disclosed in the examples that follow represent approaches the inventors have found function well in the practice of the invention, and thus can be considered to constitute examples of modes for its practice. However, those of skill in the art should, in light of the present disclosure, appreciate that many changes can be made in the specific embodiments that are disclosed and still obtain a like or similar result without departing from the spirit and scope of the invention. It shall be understood that any method described in an example may or may not have been actually performed, or any composition described in an example may or may not have been actually been formed, regardless of verb tense used.

Example 1

Ex Vivo Modulation of Cranial Suture Morphogenesis by CCN2/CTGF

Calvaria, including frontal and parietal bones with intervening interfrontal, coronal and sagittal sutures with intact dura mater, were harvested from post-natal day 10 (P10) male Sprague-Dawley rats (Harlan, Indianapolis, Ind.). Isolated calvaria were washed with dilute povidoneiodine (1:10, 1:100, and 1:1000) and PBS, and placed into the standard 12-well tissue culture plates covered with serum-free tissue culture medium supplemented with 1% antibiotic, 1 µg/mL gentamicin, 2 mM glutamine, 1 mM insulin, transferring and selenium (ITS), 1 mM non-essential aminoacids, 3 mM inorganic phosphate, and 100 µg/mL ascorbic acids (2.5 mg/mL) (Opperman, L. A., Passarelli, R. W., Morgan, E. P., Reintjes, M., and Ogle, R. C. 1995. Cranial sutures require tissue interactions with dura mater to resist osseous obliteration in vitro. J Bone Miner Res 10: 1978-1987). Medium was changed at every 2 days supplemented with 0 and 50 ng/mL recombinant human CCN2/CTGF. The concentration of CCN2/CTGF for tissue culture was selected to meet experimental conditions based on a pilot study (data not shown). 5 to 25 days following CCN2/CTGF treatment, Tn-C contents in tissue cultured medium were assayed using ELISA (IBL-America, Minneapolis, Minn.). All posterior interfrontal sutures cultured for 25 days were sagittally sectioned for histological observation (H&E staining). Suture structures were reconstructed in 3D from scanned images by µCT (vivaCT 40; Scanco Inc., Southeastern, Pa.). The thickness of each posterior interfrontal (IF) suture was measured from the 3D reconstructed models.

Example 2

Immunohistochemistry

Expressions of fibroblastic differentiation markers, vimentin and fibroblastic specific protein 1 (FSP1), in the cranial sutures were assayed by immunohistochemistry. Briefly, the harvested PIF sutures were sectioned in 4 µm thickness, deparaffinized and rehydrated in graded ethanol baths. Heat-induced epitope retrieval was performed using a pressure cooker with 10 mM citrate buffer, followed by boiling for 10 min in microwave. Upon cooling for 30 min, the sections were washed in dH$_2$O three times for 5 min each. Sections were then incubated in 3% hydrogen peroxide for 10 min, and blocked in 10% normal serum with 1% BSA for 20 min. Samples were incubated with diluted primary antibodies of vimentin (Abcam, Cambridge, Mass.) and FSP1 (Santa Cruz Biotechnology, Santa Cruz, Calif.) for 90 min. Following series of washings, biotinylated secondary antibodies (Dako, Carpinteria, Calif.) were applied for 30 min. To amplify signals, the sections were treated with avidin-biotin complex (ABC). All images were then obtained by DFC340 FX Digital Camera with DM5000 fluorescence microscope system (Leica Microsystem, Bannockburn, Ill.).

Example 3

Quantitative Expressions of TGFβ2 and Osteocalcin

As markers for synostosing suture, the expressions of TGFβ2 and osteocalcin in posterior interfrontal (PIF) suture were quantified using an infrared imaging system (Odyssey®; LI-COR, Lincoln, Nebr.). Briefly, tissue sections were washed with 0.1% Triton-X and incubated with monoclonal antibodies: TGFβ2 or osteocalcin (Abcam, Cambridge, Mass.) for 1.5 hrs at room temperature. Secondary antibodies with infrared fluorepores of Alexa Fluor® 680 (Invitrogen, Carlsbad, Calif.) and IRDye®800CW (LI-COR, Lincoln, Nebr.) were diluted in 1:100. Upon 1 hr incubation with the secondary antibodies and washing with 0.1% Tween-20 (Sigma, St. Louis, Mo.), samples were scanned and the immunoreactivities of TGFβ2 and osteocalcin were quantified using Odyssey® with 700 nm and 800 nm excitation/emission wave lengths. Integrated intensity of fluorescence per selected area of suture was calculated as the relative immunoreactivity. For in vivo samples, osteopontin (Abcam, Cambridge, Mass.) expression was examined instead of osteocalcin.

Example 4

Preparation of CCN2/CTGF-Encapsulated PLGA Microspheres

For a sustained release of CCN2/CTGF in vivo, poly-d-l-lactic-co-glycolic acid (PLGA) microspheres were used as a delivery vehicle prepared by double-emulsion technique (Lu, L., Yaszemski, M. J., and Mikos, A. G. 2001. TGF-beta1 release from biodegradable polymer microparticles: its effects on marrow stromal osteoblast function. J Bone Joint Surg Am 83-A Suppl 1: S82-91; Moioli, E. K., Hong, L., Guardado, J., Clark, P. A., and Mao, J. J. 2006. Sustained release of TGFbeta3 from PLGA microspheres and its effect on early osteogenic differentiation of human mesenchymal stem cells. Tissue Eng 12: 537-546). Briefly, a total of 250 mg PLGA was dissolved into 1 mL dichloromethane, and 10 µg of recombinant human CCN2/CTGF was diluted in 50 µL of reconstituting solution per manufacturer protocol and added to the PLGA solution, forming a mixture (primary emulsion) that was emulsified for 1 min (water-in-oil). The primary emulsion was then added to 2 mL of 1% polyvinyl alcohol (PVA, 30,000-70,000 MW), followed by 1 min mixing ([water-in-oil]-in-water). Upon adding 100 mL PVA solution, the mixture was stirred for 1 min. A total of 100 mL of 2% isopropanol was added to the final emulsion and continuously stirred for 2 h under chemical hood to remove the solvent. Control microspheres (empty and without CCN2/CTGF) were fabricated using the same procedures, with the exception of using 50 μL distilled water instead of the CCN2/CTGF solution. Empty microspheres containing only water as controls were implemented to subtract the possible effects of degradation byproducts of PLGA alone. PLGA microspheres containing CCN2/CTGF or distilled water were isolated using filtration (2 μm filter) and washed with distilled water. Microspheres were frozen in liquid nitrogen for 30 min and lyophilized for 48 h. Freeze-dried PLGA microspheres were stored at −20° C. prior to use.

Example 5

Controlled Release of Microencapsulated CCN2/CTGF

To determine entrapment yield, 10 mg of CCN2/CTGF-encapsulating PLGA microspheres were dissolved in 1 mL of chloroform, and 1 mL of 1% BSA solution was added. Mixtures were allowed to settle for 6 hrs, and CCN2/CTGF-rich solution was collected for quantification. Concentration of CCN2/CTGF in the solution was measured using Fluorophore-Linked Immunosorbent Assay (FLISA). Briefly, 2 μg/mL CCN2/CTGF antibody (ab6992, Abcam, Cambridge, Mass.) in 0.02% sodium azide was allowed to bind on 96-well polystyrene microplate by incubating at 37° C. for 30 min, room temperature for 2 hrs with gentle agitation. After washing 3 times with 0.05% Tween®-20 (Sigma, St. Louis, Mo.), each well was treated with Odyssey Blocking Buffer (LI-COR, Lincoln, Nebr.) for 1 hr. Then samples/standards dilutions were added in each well, followed by incubation at RT for 2 hrs. Following 3 times washes, detection antibody (IRDye™ 680, LI-COR, Lincoln, Nebr.) was pipetted into each well. Incubated at RT for 1 hr and additional washes, the plate was scanned at 700 nm excitation/emission using an automated infrared imaging system (Odyssey®; LI-COR, Lincoln, Nebr.) with the following parameters: 200 μm in resolution, 3.0 mm focus offset, and intensity setting of 7. Quantitative CCN2/CTGF concentrations were calculated from integrated intensity of fluorescence on each well, comparing to standard curve. For in vitro CCN2/CTGF release profile, 10 mg of the PLGA microspheres were dispersed in 1 mL of 1% BSA and continuously agitated at 60 rpm and 37° C. From 3 days to 6 wks, the entire amount of supernatants was collected periodically, and the CCN2/CTGF concentration was quantitatively measured using FLISA as described above. CCN2/CTGF release rate was expressed as a percentage of the total CCN2/CTGF/mg PLGA microspheres.

Example 6

In Vivo Cranial Suture Regeneration by Controlled Release of CCN2/CTGF 12 wks-old Sprague-Dawley rats with fully synostosed cranial suture were used. Briefly, rats were anesthetized using inhalation of isoflurane at 1-5% within an enclosed chamber. A 2 cm-long linear cut was made to expose the skull bone. Then the synostosed posterior interfrontal suture was removed with 2×4 mm surrounding bone using a dental bur with irrigation of phosphate buffered saline. Then a previously shaped-to-size collagen sponge (Integra, Plainsboro, N.J.) containing 10 mg of the CCN2/CTGF-encapsulated PLGA or empty PLGA microspheres replaced the synostosed cranial suture. At 4 wks post-op, tissues were harvested and analyzed by μCT. The harvested tissues were sectioned in 4 μm thickness and prepared for histological observation including H&E staining and immunohistochemistry.

Example 7

Statistics

Results were analyzed using a one-way analysis of variance (ANOVA) with post-hoc Bonferroni tests to determine significant differences between or within groups, using a statistical package (SPSS, Chicago, Ill.). Results were considered significant if a value of $p<0.05$ was attained.

Example 8

Ex Vivo Modulation of Tissue Morphogenesis by CCN2/CTGF

Methods are according to those described in Examples 1-7 unless specified otherwise.

Entire calvaria including periosteum and the underlying dura mater were isolated from p10 (postnatal day 10) Sprague-Dawley rats and cultured in 12-well plates with 50 ng/mL CCN2/CTGF-conditioned medium using a previously established model (Opperman, L. A., Passarelli, R. W., Morgan, E. P., Reintjes, M., and Ogle, R. C. 1995. Cranial sutures require tissue interactions with dura mater to resist osseous obliteration in vitro. J Bone Miner Res 10: 1978-1987). The rat posterior interfrontal suture is a well established craniosynostosis model and undergoes synostosis between approximately p20 to p30 days (Slater, B. J., Lenton, K. A., Kwan, M. D., Gupta, D. M., Wan, D. C., and Longaker, M. T. 2008. Cranial sutures: a brief review. Plast Reconstr Surg 121: 170e-178e; Collins, J. M., Ramamoorthy, K., Da Silveira, A., Patston, P., and Mao, J. J. 2005. Expression of matrix metalloproteinase genes in the rat intramembranous bone during postnatal growth and upon mechanical stresses. J Biomech 38: 485-492; Moss, M. L. 1954. Growth of the calvaria in the rat; the determination of osseous morphology. Am J Anat 94: 333-361).

CTGF treatment for 25 days resulted in marked suture patency between mineralized bones (see e.g., FIG. 1C, in comparison with virtual disappearance of suture mesenchyme CTGF treatment (see e.g., FIG. 1B).

At p10, the representative cranial suture showed clear presence of patent suture mesenchyme between trabecular bone on both sides (see e.g., FIG. 1A). Following 25 days in organ culture, the representative p35 suture without CCN2/CTGF treatment showed a clear trend of synostosis with virtual disappearance of suture mesenchyme (see e.g., FIG. 1B). In contrast, exposure of 50 ng/mL recombinant human CCN2/CTGF to the representative p10 cranial suture explant for 20 days led to continuing presence of suture mesenchyme by p35 (see e.g., FIG. 1C).

Example 9

CCN2/CTGF Promotes Fibroblastic Differentiation Ex Vivo

Methods are according to those described in Examples 1-7 unless specified otherwise.

CTGF treatment for 25 days resulted in marked suture patency between mineralized bones (see e.g., FIG. 1C, in comparison with virtual disappearance of suture mesenchyme CTGF treatment (see e.g., FIG. 1B). Immunohistochemistry for fibroblast-specific protein-1 (FSP1) (see e.g., FIG. 1D, FIG. 1E, FIG. 1F) and vimentin (see e.g., FIG. 1G, FIG. 1H, FIG. 1I) of organ cultured cranial sutures for 20 days. FSP1 and vimentin expression is strong in the representative p10 and CTGF-treated p35 suture specimens (see e.g., FIG. 1D, FIG. 1F and FIG. 1G, FIG. 1I), in comparison with the representative specimens without CTGF treatment (see e.g., FIG. 1E, FIG. 1H).

Figures 1D, 1E, 1F:
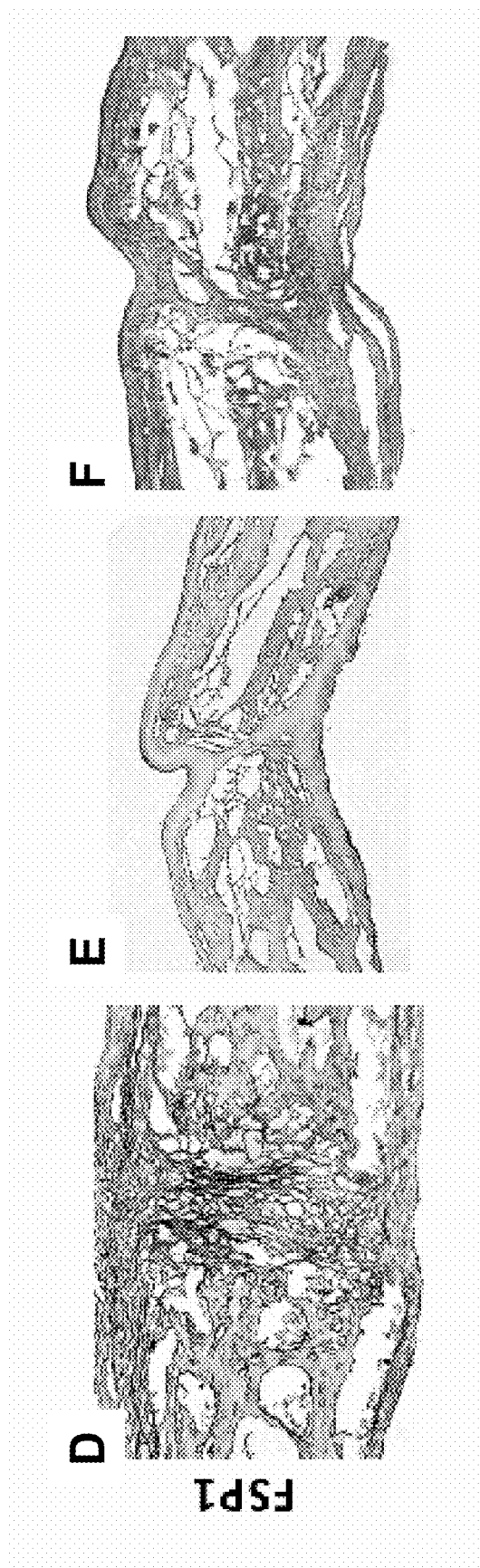
In FIG. 1D-F, darker grey to light black areas correspond to FSP1 staining. Micrographs of immunohistochemistry stain for vimentin through the native interfrontal suture by postnatal day 10 or p10 (FIG. 1G), p25 suture without CTGF delivery (FIG. 1H), and p25 suture with 50 ng/mL CTGF (FIG. 1I). Scale: 60 μm.
Figures 1G, 1H, 1I:
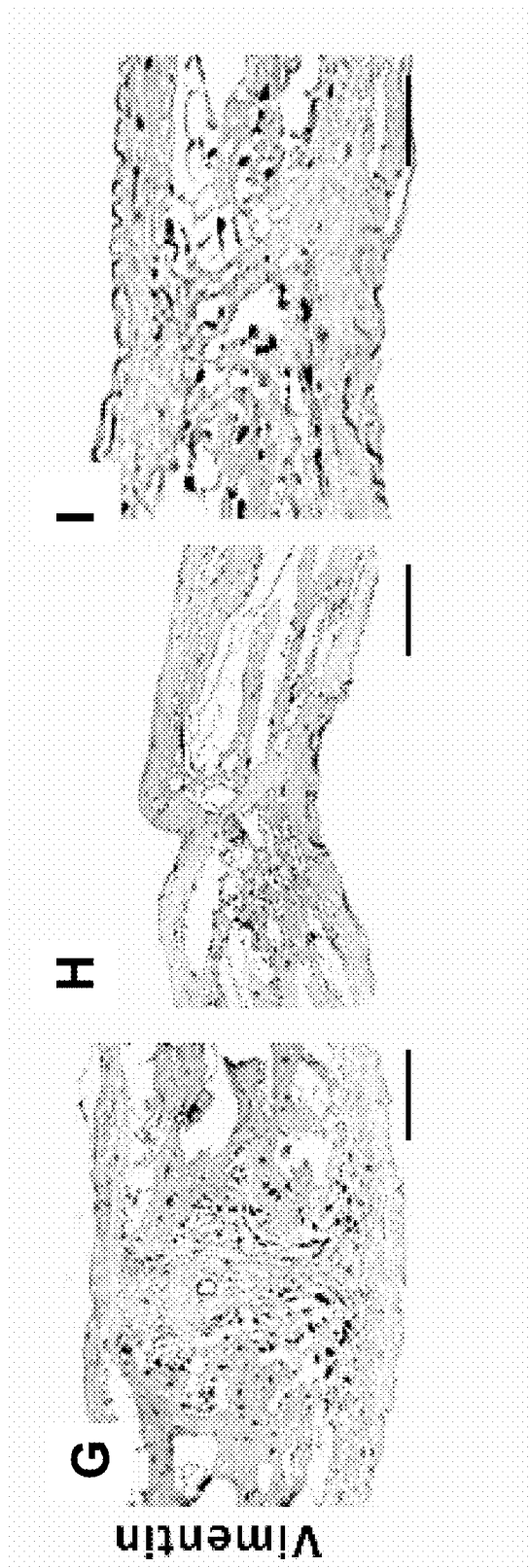
In FIG. 1G-I, light black to black areas correspond to vimentin staining. For additional details regarding methodology, see Examples 8-9.

Cells positive of fibroblast specific protein-1 (FSP1), a fibroblast differentiation marker, were primarily immunolocalized in suture mesenchyme, dura mater and periosteum in the representative P10 specimen (see e.g., FIG. 1D). With advancing synostosis by p35, FSP1 positive cells primarily immunolocalized in periosteum and dura, but scarcely in suture mesenchyme (see e.g., FIG. 1E). By p35 following 50 ng/mL CCN2/CTGF treatment of a representative P10 specimen, FSP1-positive cells were abundant in suture mesenchyme as well as the periosteum and dura mater (see e.g., FIG. 1F), somewhat similar to p10 (see e.g., FIG. 1D). Furthermore, cells positive of vimentin, another fibroblast differentiation marker, were primarily immunolocalized to suture mesenchyme (see e.g., FIG. 1G). In contrast, there were few vimentin-positive cells in the representative synostosed suture by p35 without CCN2/CTGF treatment (see e.g., FIG. 1H). Following 50 ng/mL CCN2/CTGF treatment for 20 days, the distribution of vimentin positive cells was remarkably similar at p35 (see e.g., FIG. 1I) to the p10 specimen (see e.g., FIG. 1G). The distribution of both FSP1 and vimentin ex vivo provides important clues for CCN2/CTGF's role in promoting fibrogenesis in cranial suture.

Example 10

CCN2/CTGF Maintains Sutural Patency Ex Vivo and Increases Tenascin C Content

Methods are according to those described in Examples 1-7 unless specified otherwise.

Without CTGF treatment, the representative interfrontal suture narrowed by post-natal day 35 (p35). Treatment with 50 ng/mL CTGF resulted in sutural patency in the representative p35 specimen. Quantitatively, suture width is significantly greater with CTGF treatment than without CTGF, from 3D reconstructed calvarial structures by µCT. The average tenascin-C content (Tn-C) of CTGF treated cranial sutures is significantly greater than without CTGF treatment (n=3, *: $p<0.05$), indicating that CTGF promotes fibrogenesis.

Figure 2A:
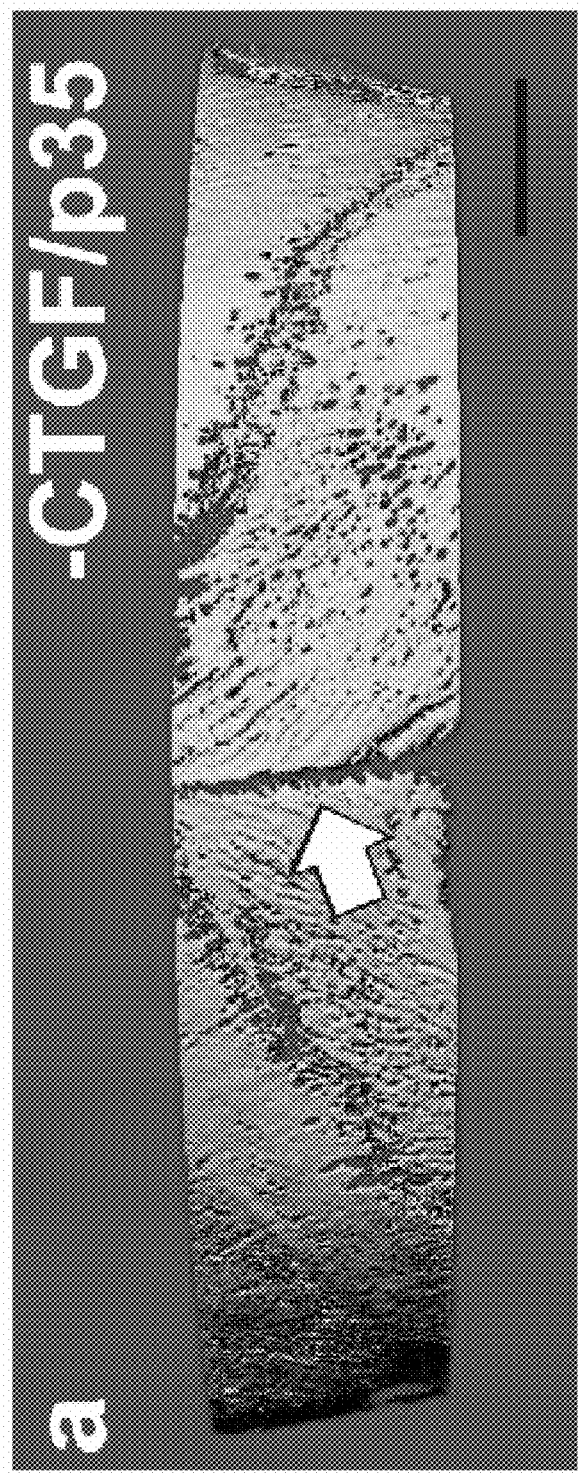
FIG. 2A shows suture patency by microcomputed tomography (μCT) without CTGF treatment at p35.
Figure 2B:
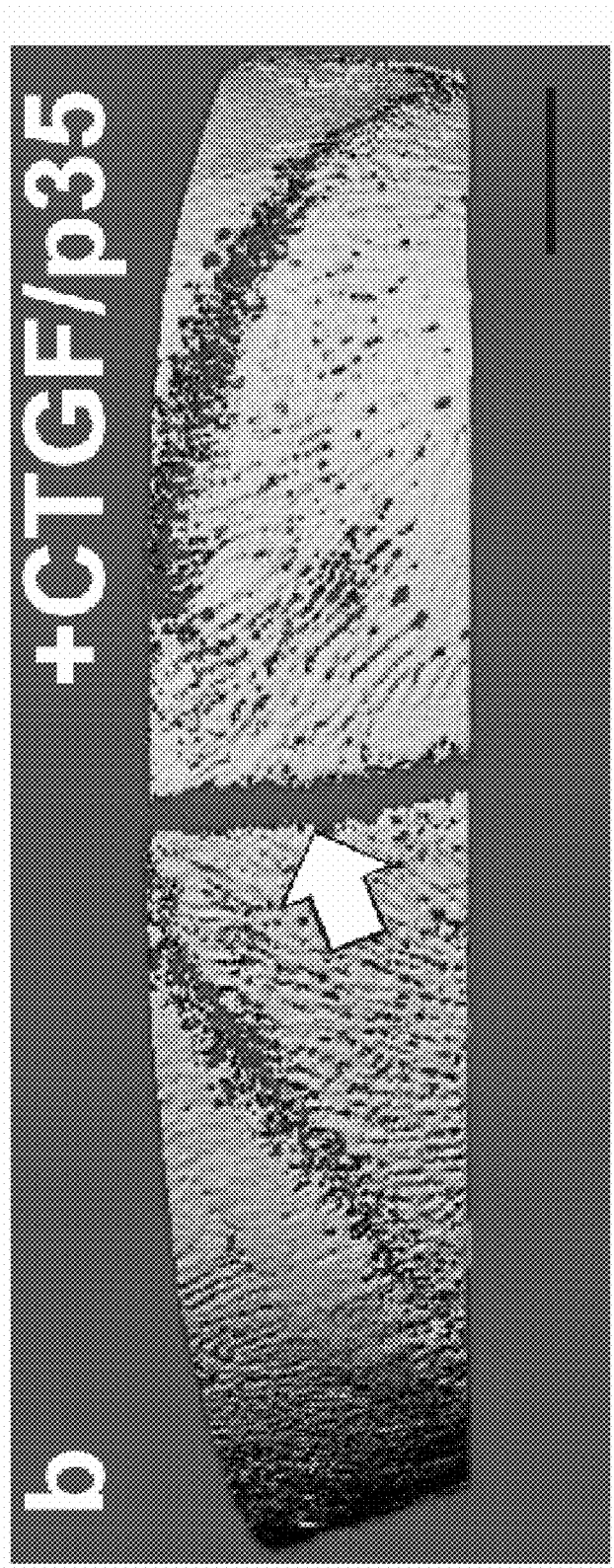
FIG. 2B shows suture patency by microcomputed tomography (μCT) with CTGF treatment at p35.
Figure 2D:
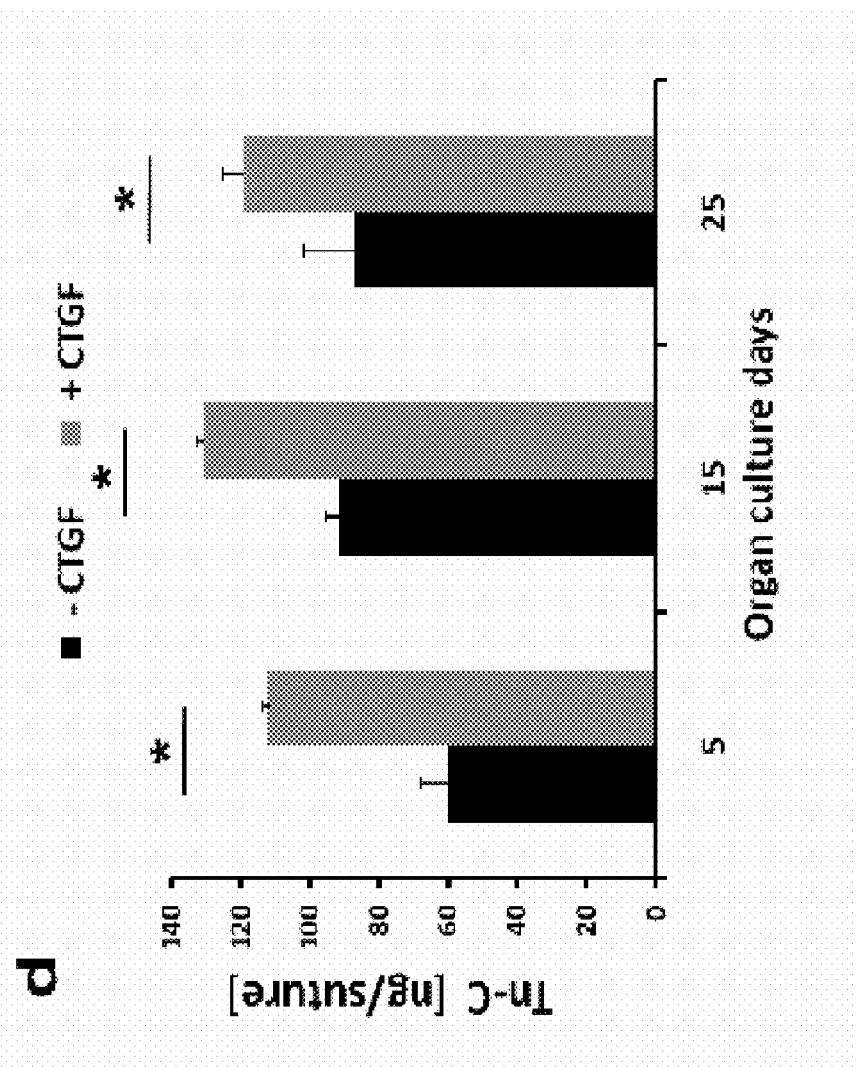
FIG. 2D shows suture tenascin-C content (ng/structure) for −CTGF and +CTGF as a function of organ culture days. Data are represented as mean±SD. Scale: 1 mm. For additional details regarding methodology, see Example 10.

In comparison with the narrowing of the representative suture specimen cultured without CCN2/CTGF treatment (see e.g., FIG. 2A), the representative CCN2/CTGF-treated specimen by p35 was patent (see e.g., FIG. 2B). The average width of CCN2/CTGF-treated cranial sutures at 290±79 µm was significantly greater, by approximately 3 fold, than cranial sutures without CCN2/CTGF at 92±84 µm, indicating that CCN2/CTGF delivery alone is sufficient to maintain sutural patency. This quantitative analysis was achieved by reconstructing multiple calvarial specimens by microcomputed tomography (µCT) (see e.g., FIG. 2C) (n=5; $p<0.01$). The molecular content of tenascin-C, another fibroblastic differentiation marker, was significantly greater in CCN2/CTGF-treated specimens than those without CCN2/CTGF treatment (see e.g., FIG. 2D) (n=5; $p<0.05$), by subjecting harvested sutural tissue to ELISA analysis.

Example 11

CCN2/CTGF Suppresses TGFβ2 and Osteocalcin Expression Ex Vivo

Methods are according to those described in Examples 1-7 unless specified otherwise.

Figures 3A, 3B, 3C, 3D, 3E, 3F:
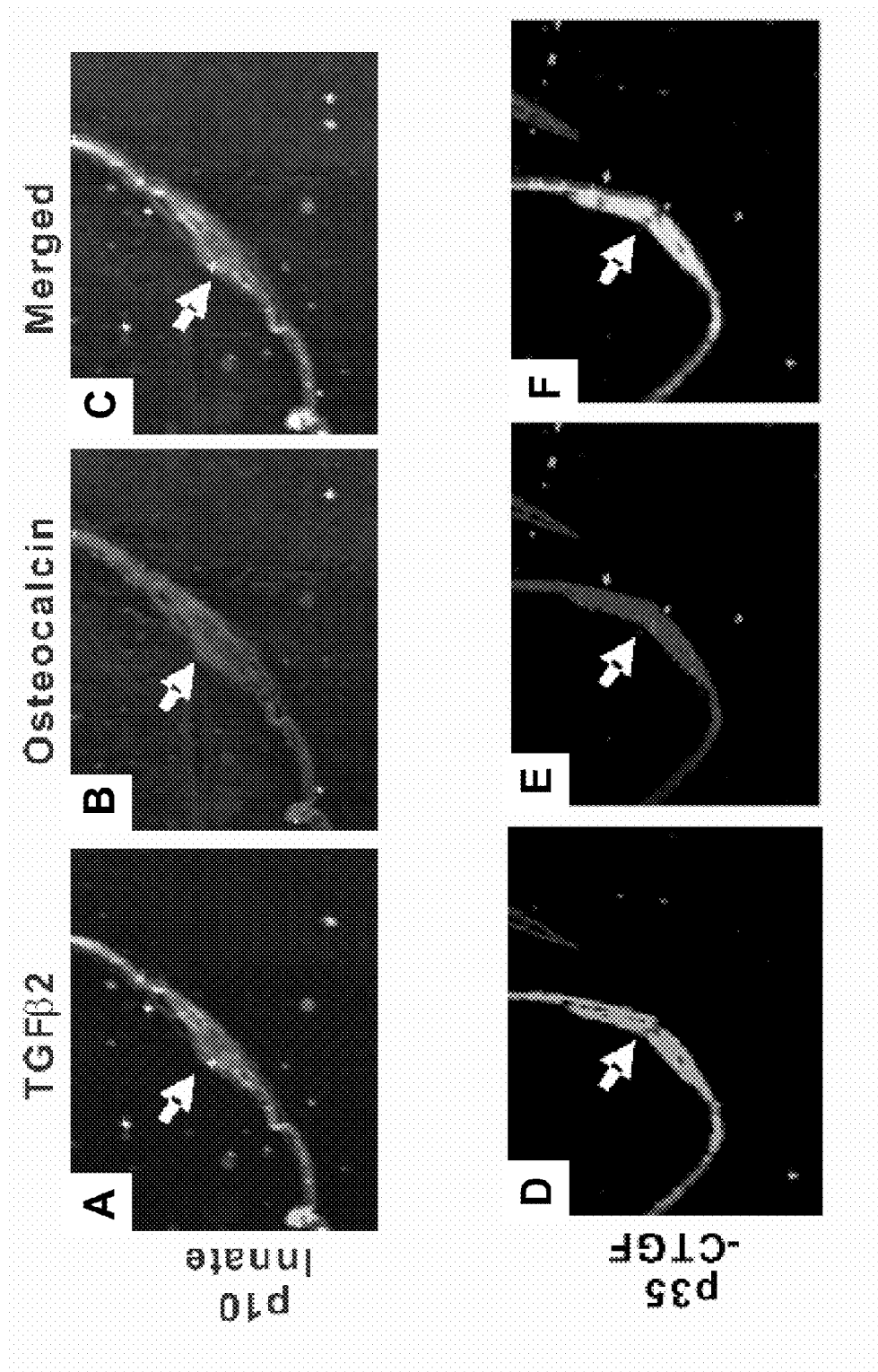
FIG. 3A shows p10 innate with TGFβ2 marker. White to light grey areas correspond to TGFβ2 marker.
FIG. 3B shows p10 innate with Osteocalcin marker. Light grey to medium grey areas correspond to osteocalcin marker.
FIG. 3C shows a merged image of FIG. 3A and FIG. 3B. Generally, TGFβ2 marker appears white to light grey and osteocalcin marker appears light grey to medium grey.
FIG. 3D shows p35 without CTGF treatment with TGFβ2 marker. White to light grey areas correspond to TGFβ2 marker.
FIG. 3E shows p35 without CTGF treatment with Osteocalcin marker. Light grey to medium grey areas correspond to osteocalcin marker.
FIG. 3F shows a merged image of FIG. 3D and FIG. 3E. Generally, TGFβ2 marker appears white to light grey and osteocalcin marker appears light grey to medium grey.
Figures 3G, 3H, 3I:
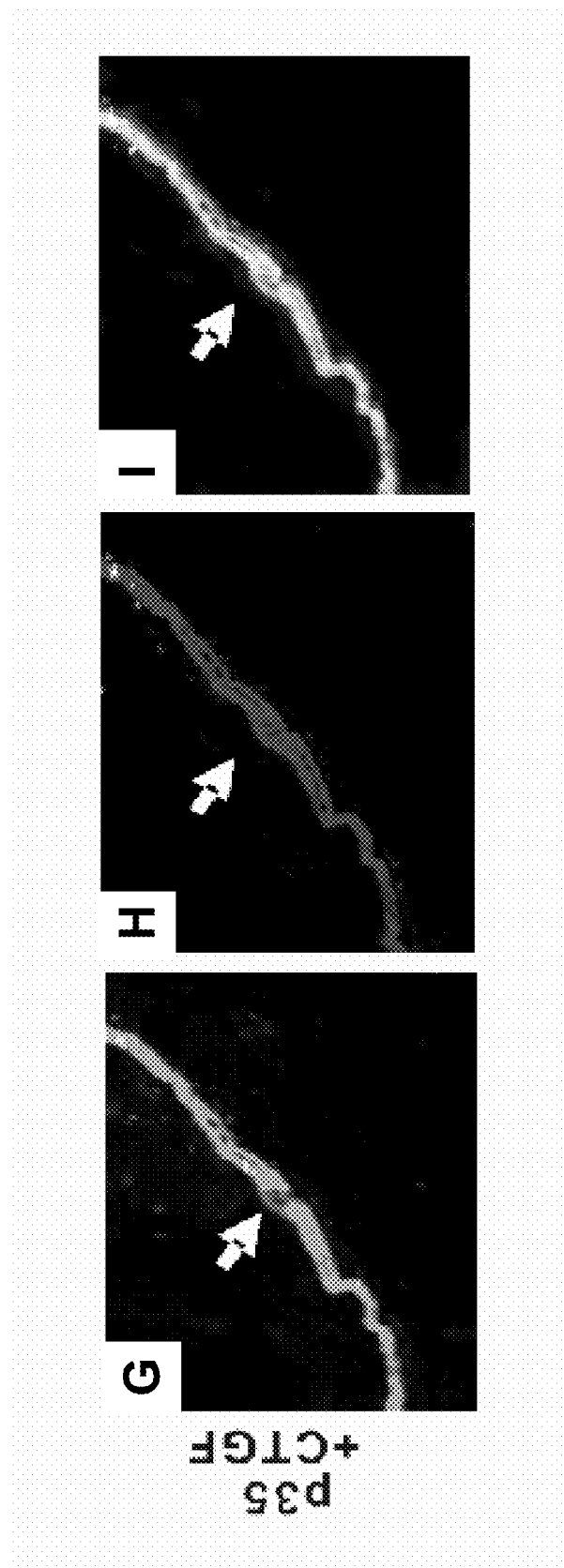
FIG. 3G shows p35 with CTGF treatment with TGFβ2 marker. White to light grey areas correspond to TGFβ2 marker.
FIG. 3H shows p35 with CTGF treatment with Osteocalcin marker. Light grey to medium grey areas correspond to osteocalcin marker.
FIG. 3I shows a merged image of FIG. 3G and FIG. 3H. Generally, TGFβ2 marker appears white to light grey and osteocalcin marker appears light grey to medium grey. Arrows point to suture mesenchyme. For additional details regarding methodology, see Example 11.
Figures 3J, 3K:
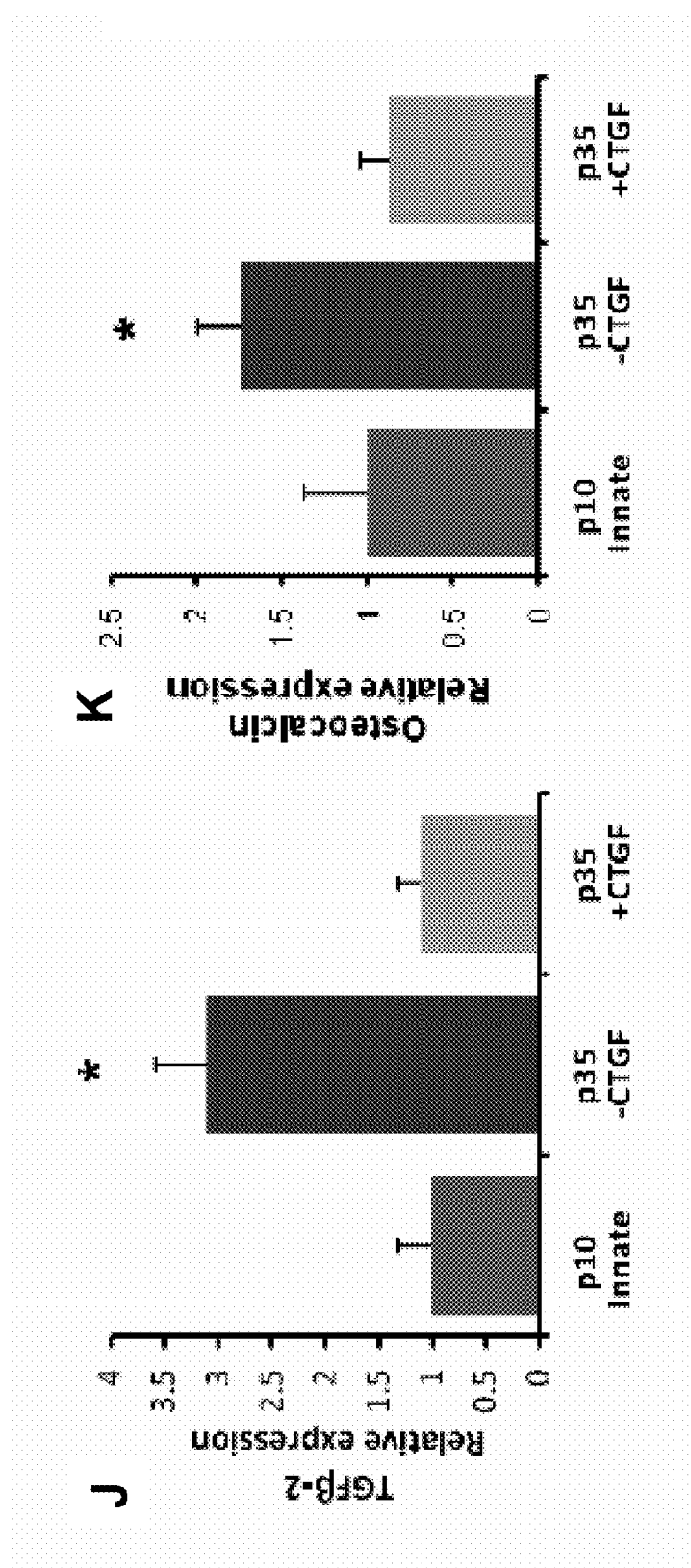
FIG. 3 is a series of immunofluorescence images and a pair of bar graphs for TGFβ2 and osteocalcin with or without CTGF treatment.

TGFβ2 is moderate in post-natal day 10 suture (p10) (see e.g., FIG. 3A), and remarkably enhanced by p35 at which time suture synostosis occurred (see e.g., FIG. 3B), but substantially diminished with CTGF treatment by p35, especially in suture mesenchyme (see e.g., FIG. 3G). Arrows point to suture mesenchyme. Osteocalcin expressions showed somewhat similar patterns at p10 (see e.g., FIG. 3B), p35 without CTGF (see e.g., FIG. 3E) and p35 with CTGF (see e.g., FIG. 3F). Merged images are shown in FIG. 3C, FIG. 3F, FIG. 3I, indicating somewhat co-localization of TGFβ2 and osteocalcin. Quantitatively, significant enhancement in TGFβ2 and osteocalcin by p35 over p10 suture specimens was remarkably attenuated by CTGF treatment, respectively in (see e.g., FIG. 3I, FIG. 3K) ($p<0.05$; n=5).

In the representative innate p10 specimen, TGFβ2 expression was throughout the specimen (see e.g., FIG. 3A). Without CCN2/CTGF treatment, TGFβ2 expression was exceedingly strong in calvarial plates in the synostosed p35 suture with suture mesenchyme barely recognizable (see e.g., FIG. 3D). In contrast, the representative CCN2/CTGF-treated p35 specimen showed remarkably weak TGFβ2 expression in the patent suture mesenchyme but somewhat strong TGFβ2 expression in calvarial bone plates (see e.g., FIG. 3G). The expression of osteocalcin, a late osteogenesis marker (Liu, F., Malaval, L., Gupta, A. K., and Aubin, J. E. 1994. Simultaneous detection of multiple bone-related mRNAs and protein expression during osteoblast differentiation: polymerase chain reaction and immunocytochemical studies at the single cell level. Dev Biol 166: 220-234; Yao, K. L., Todescan, R., Jr., and Sodek, J. 1994. Temporal changes in matrix protein synthesis and mRNA expression during mineralized tissue formation by adult rat bone marrow cells in culture. J Bone Miner Res 9: 231-240), was also broad in the representative p10 innate specimen (see e.g., FIG. 3B). Without CCN2/CTGF, osteocalcin expression was strong throughout the representative synostosing p35 specimen (see e.g., FIG. 3E), virtually obliterating suture mesenchyme. In contrast, the representative CCN2/CTGF-treated specimen showed weak osteocalcin expression in suture mesenchyme but strong expression in the rest of calvarial bones (see e.g., FIG. 3H). Upon overlay, TGFβ2 and osteocalcin expression were found to be somewhat co-localized (see e.g., FIG. 3C, FIG. 3F, FIG. 3I). Quantitatively, CCN2/CTGF significantly attenuated TGFβ2 and osteocalcin expression in rescued cranial sutures as compared to synostosed sutures without CCN2/CTGF treatment (see e.g., FIG. 3J, FIG. 3K).

Example 12

Microencapsulation of CCN2/CTGF for Sustained Release Kinetics

The discovery of CCN2/CTGF's novel action in the modulation of sutural synostosis ex vivo was extended into a well established in vivo model of craniosynostosis (Shi-Wen, X., Leask, A., and Abraham, D. 2008. Regulation and function of connective tissue growth factor/CCN2 in tissue repair, scarring and fibrosis. Cytokine Growth Factor Rev 19: 133-144). Bioactive cues such as peptides and proteins delivered conventionally by injection are known to undergo premature denaturation and diffusion away from the intended target (Lu, L., Yaszemski, M. J., and Mikos, A. G. 2001. TGF-beta1 release from biodegradable polymer microparticles: its effects on marrow stromal osteoblast function. J Bone Joint Surg Am 83-A Suppl 1: S82-91; Moioli, E. K., Hong, L., Guardado, J., Clark, P. A., and Mao, J. J. 2006. Sustained release of TGFbeta3 from PLGA microspheres and its effect on early osteogenic differentiation of human mesenchymal stem cells. Tissue Eng 12: 537-546). CCN2/CTGF was encapsulated in PLGA microspheres for protection against premature diffusion and denaturation by double-emulsion (Moioli et al, 2006) and delivered CCN2/CTGF by controlled release.

Figures 4A, 4B:
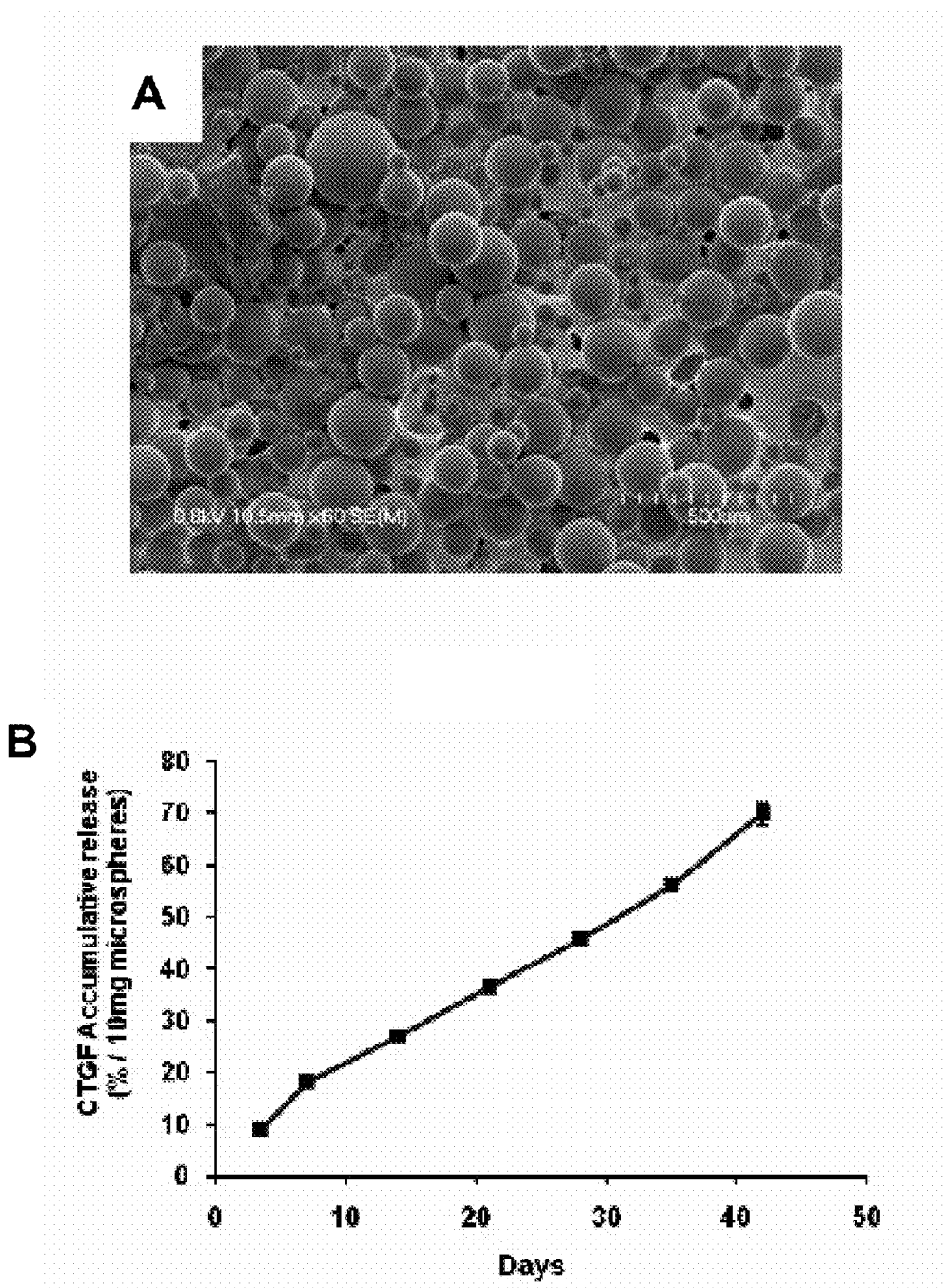
FIG. 4A is an SEM image showing CTGF microencapsulated in biocompatible and biodegradable PLGA particles.
FIG. 4B is a line and scatter plot showing CTGF accumulative release (%/10 mg microspheres) as a function of time (days).

The average diameter of CCN2/CTGF-encapsulating PLGA microspheres was 120±64 μm by SEM analysis (see e.g., FIG. 4A). Release kinetics of CCN2/CTGF were determined using Fluorophore-Linked Immunosorbent Assay (FLISA). Microencapsulated CCN2/CTGF showed a sustained release profile for the tested 6 wks with approximately 18% released within the first week, followed by nearly 10% continuous release per week (see e.g., FIG. 4B). After 6 wks, approximately 70% of the total encapsulated CCN2/CTGF was released. The release kinetics can be fine-tuned per biological need (Lu, L., Yaszemski, M. J., and Mikos, A. G. 2001. TGF-beta1 release from biodegradable polymer microparticles: its effects on marrow stromal osteoblast function. J Bone Joint Surg Am 83-A Suppl 1: S82-91; Moioli, E. K., Hong, L., Guardado, J., Clark, P. A., and Mao, J. J. 2006. Sustained release of TGFbeta3 from PLGA microspheres and its effect on early osteogenic differentiation of human mesenchymal stem cells. Tissue Eng 12: 537-546).

Example 13

CCN2/CTGF-Mediated Fibrogenesis In Vivo

CTGF delivery leading to restoration of cranial suture morphogenesis.

Craniotomy, a highly invasive surgery, is currently performed to resect synostosed cranial suture(s) and re-shape multiple calvarial bones in the craniosynostosis patient. To explore whether CCN2/CTGF has novel effects on minimizing surgical trauma by regenerating cranial sutures, a well established in vivo craniosynostosis model was utilized (Shi-Wen, X., Leask, A., and Abraham, D. 2008. Regulation and function of connective tissue growth factor/CCN2 in tissue repair, scarring and fibrosis. Cytokine Growth Factor Rev 19: 133-144).

Methods are according to those described in Examples 1-7 unless specified otherwise.

The posterior interfrontal suture in Sprague-Dawley rat is synostosed within 35 days postnatal (Slater, B. J., Lenton, K. A., Kwan, M. D., Gupta, D. M., Wan, D. C., and Longaker, M. T. 2008. Cranial sutures: a brief review. Plast Reconstr Surg 121: 170e-178e; Collins, J. M., Ramamoorthy, K., Da Silveira, A., Patston, P., and Mao, J. J. 2005. Expression of matrix metalloproteinase genes in the rat intramembranous bone during postnatal growth and upon mechanical stresses. J Biomech 38: 485-492; Moss, M. L. 1954. Growth of the calvaria in the rat; the determination of osseous morphology. Am J Anat 94: 333-361). In 12-wk-old Sprague-Dawley rats, the synostosed interfront suture was resected with surrounding bone (2×4 mm), while preserving the integrity of dura mater (Moioli, E. K., Clark, P. A., Sumner, D. R., and Mao, J. J. 2008. Autologous stem cell regeneration in craniosynostosis. Bone 42: 332-340; Hong, L., and Mao, J. J. 2004. Tissue-engineered rabbit cranial suture from autologous fibroblasts and BMP2. J Dent Res 83: 751-756). A 2×4 mm collagen sponge infused with microencapsulated CCN2/CTGF replaced the resected cranial suture.

Figure 4C:
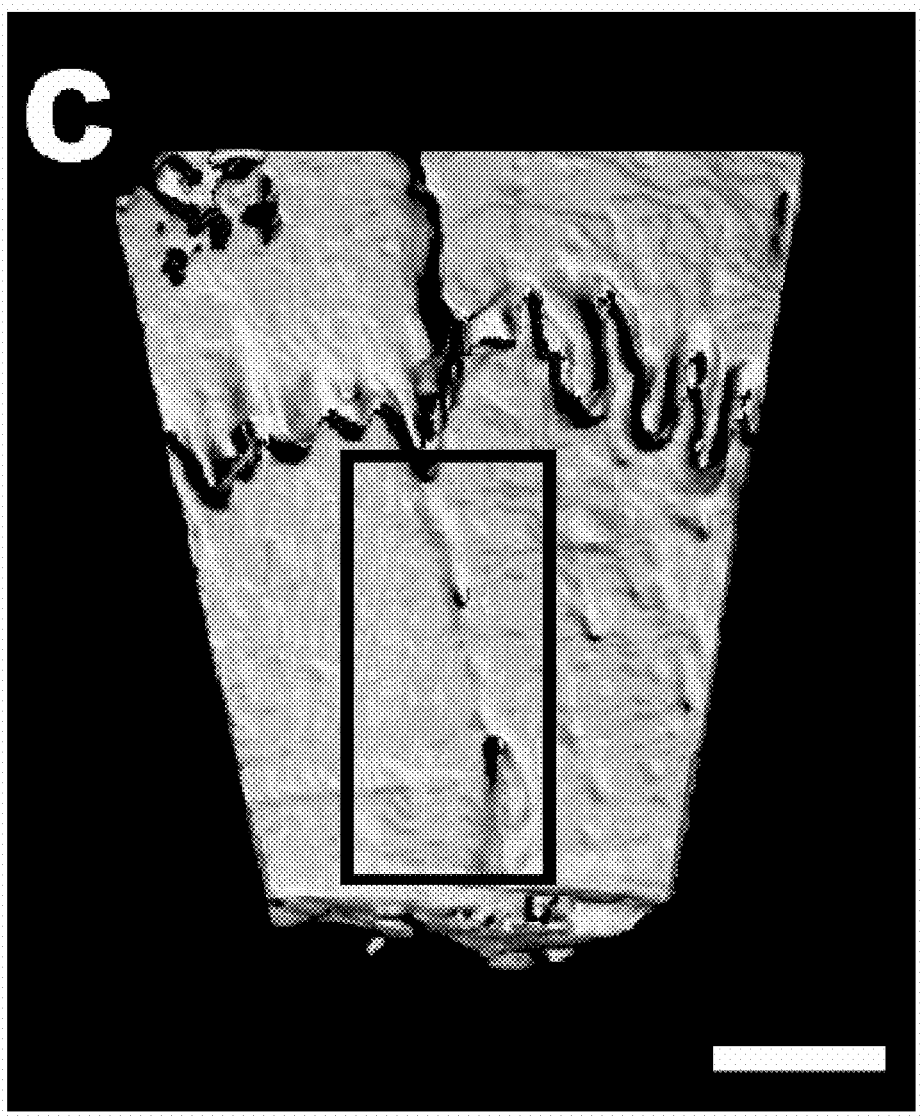
FIG. 4C microcomputed tomography image showing interfrontal suture without CTGF treatment at post-natal day 35 (p35). Scale: 1 mm.
Figure 4D:
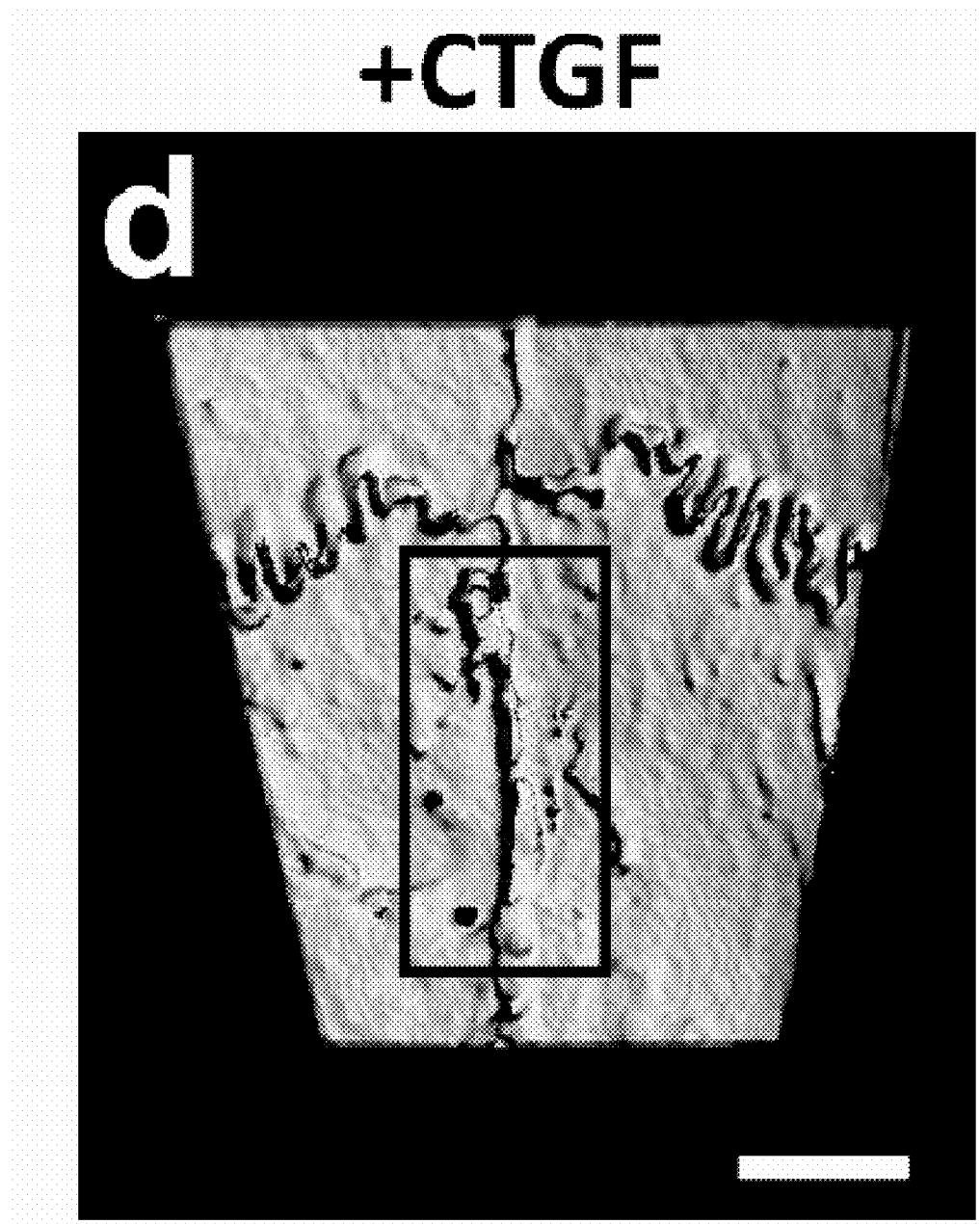
FIG. 4D microcomputed tomography image showing interfrontal suture with CTGF treatment at post-natal day 35 (p35). Scale: 1 mm.

The interfrontal suture undergoes synostosis by post-natal day 35 (p35). FIG. 4C shows virtual synostosis of p35, native suture as shown in the boxed area (without in vivo CTGF delivery). FIG. 4D shows that, with in vivo delivery of microencapsulated CTGF, the interfrontal suture was regenerated, as show in the boxed area. Note that adjacent transverse coronal sutures remained patent and shows typical zig-zag course in either native p35 specimen or CTGF-treated p35 specimen (see e.g., FIG. 4C, FIG. 4D), as well as the patent sagittal or inter-parietal suture that is dorsal to the boxed interfrontal suture. Macroscopic regeneration of cranial suture is substantiated by microscopic characteristics. H&E staining showed that without in vivo CTGF delivery, synostosis readily occurred and is characterized by well mineralized bone with marrow (m) in, for example, FIG. 4E and FIG. 4G, with mature osteocytes and blood vessels populating bone marrow. In contrast, in vivo CTGF delivery by microencapsulation yielded typical cranial suture-like structures (see e.g., FIG. 4F, FIG. 4H). The high cellularity of the regenerated cranial suture (see e.g., FIG. 4H) indicates that fibrogenesis, rather than pathological fibrosis, occurred in regenerating cranial sutures. Some biodegradable microspheres have remained in the regenerated cranial suture mesenchyme (μS) and are anticipated to undergo complete degradation whose rate can be manipulated. Well mineralized bone and bone marrow are present and adjacent to the regenerated cranial suture.

Four weeks following this localized surgical replacement of synostosed cranial suture, μCT imaging showed re-occurring synostosis, remarkably in virtually the same location as the resected, synostosed cranial suture (see e.g., FIG. 4C). In contrast, control-released CCN2/CTGF orchestrated the regeneration of a cranial suture remarkably in virtually the same location as the resected, synostosed cranial suture (see e.g., FIG. 4D). The inter-parietal suture dorsal to the surgical site is referenced for morphology (see e.g., FIG. 4C, FIG. 4D). The adjacent two coronal sutures were apparently undisturbed and remained patent with (see e.g., FIG. 4D) or without (see e.g., FIG. 4C) CCN2/CTGF delivery.

Figures 4E, 4F, 4G, 4H:
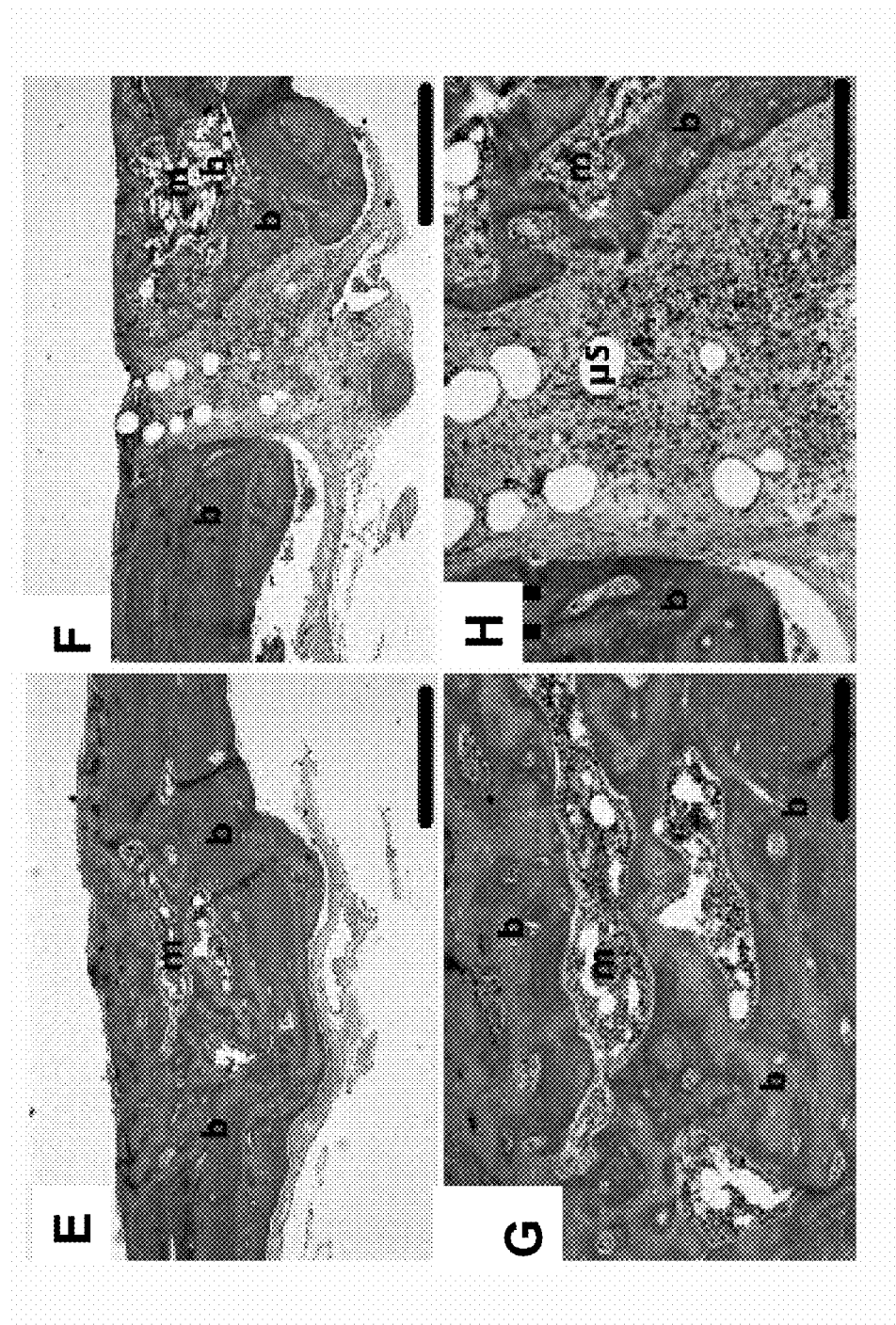
FIG. 4E is an immunofluorescence image showing H&E staining of cranial suture without in vivo CTGF delivery. b: bone; m: marrow; μs: microspheres. Scale: 500 μm.
FIG. 4F is an immunofluorescence image showing H&E staining cranial suture with in vivo CTGF delivery. b: bone; m: marrow; μs: microspheres. Scale: 500 μm.
FIG. 4G is an immunofluorescence image showing H&E staining of cranial suture without in vivo CTGF delivery. b: bone; m: marrow; μs: microspheres. Scale: 200 μm.
FIG. 4H is an immunofluorescence image showing H&E staining cranial suture with in vivo CTGF delivery. b: bone; m: marrow; μs: microspheres. Scale: 200 μm. For H&E staining images, uniformly medium grey areas correspond to eosinophilic structures, such as intracellular or extracellular protein or red blood cells; while darker grey areas correspond to basophilic structures, such as those containing nucleic acids, such as the ribosomes and the chromatin-rich cell nucleus, and the cytoplasmatic regions rich in RNA. For additional details regarding methodology, see Examples 12-13.

Microscopic observation confirmed that placebo CCN2/CTGF-free microspheres led to disappearance of suture mesenchyme and re-synostosis with well mineralized bone (see e.g., FIG. 4E, FIG. 4G). In contrast, a cranial suture was regenerated and replaced the synostosed cranial suture (see e.g., FIG. 4F, FIG. 4H). The suture mesenchyme of the representative regenerated cranial suture is continuous with both dura mater and periosteum (see e.g., FIG. 4F, FIG. 4H). Dura mater was preserved in both synostosed and regenerated sutures (see e.g., FIG. 4E, FIG. 4F), suggesting that control-released CCN2/CTGF, instead of dura mater, is the primary determinant of suture patency or synostosis. A number of biocompatible PLGA microspheres were still present in the regenerated cranial suture (see e.g., FIG. 4F, FIG. 4H), although PLGA is a biocompatible and biodegradable material whose degradation rate can be readily modulated.

Example 14

CCN2/CTGF Promotes Fibrogenesis In Vivo

Methods are according to those described in Examples 1-7 unless specified otherwise.

CTGF leads to abundant FSP1 and vimentin positive cells in the regenerated cranial suture in vivo. Without in vivo CTGF delivery, FSP1-positive cells primarily resided in bone marrow (see e.g., FIG. 5A). Contrastingly, abundant FSP1-positive cells populated suture mesenchyme of the regenerated cranial suture with CTGF delivery (see e.g., FIG. 5B). Without CTGF, little vimentin positive cells were present in the marrow of synostosed bone (see e.g., FIG. 5C). In contrast, abundant vimentin positive cells populated the mesenchyme of regenerated cranial suture (see e.g., FIG. 5D).

Figures 5A, 5B, 5C, 5D:
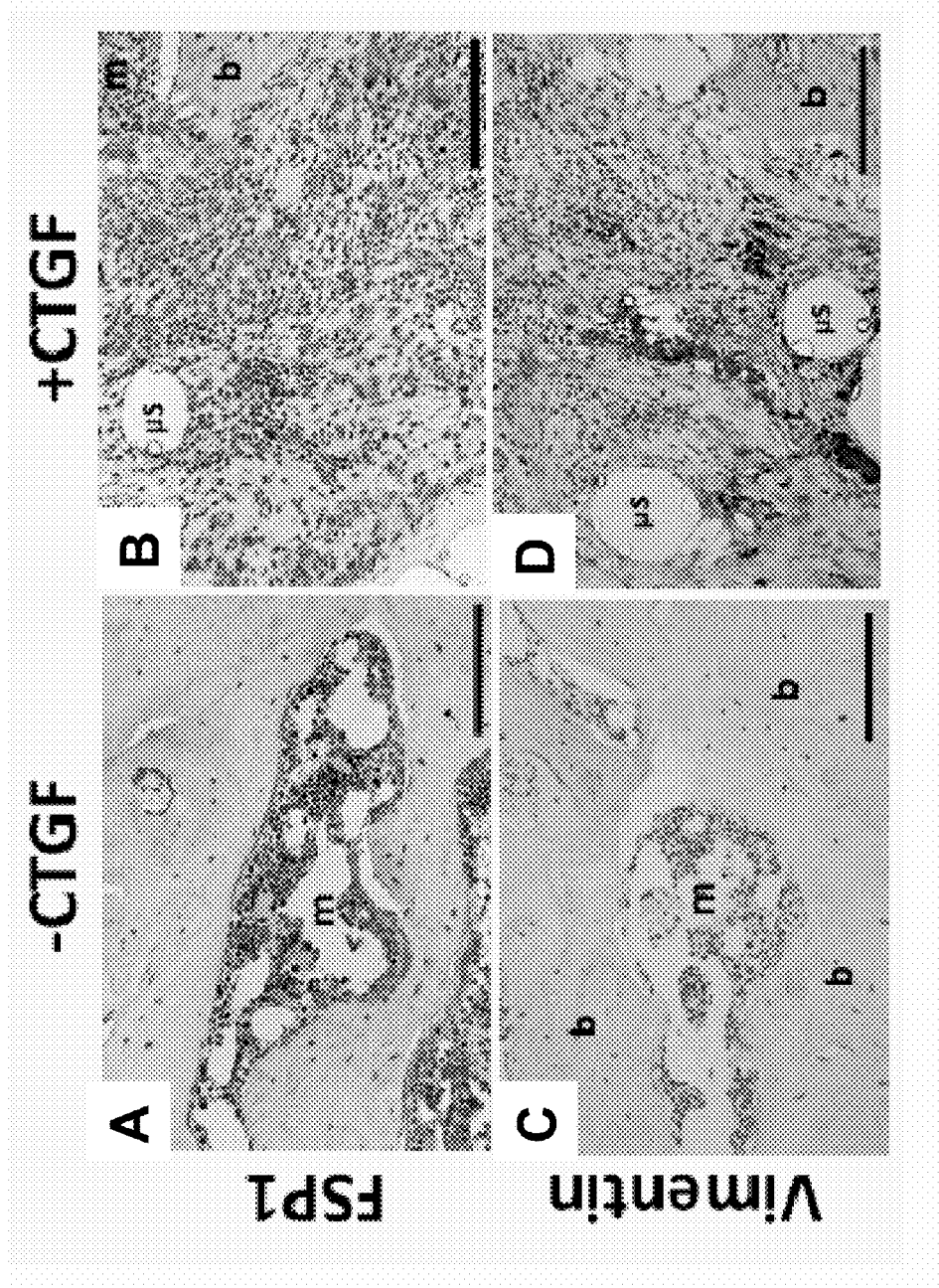
FIG. 5A shows FSP1 staining in cranial suture, including suture mesenchyme, without in vivo CTGF delivery. m: marrow. Scale: 100 μm.
FIG. 5B shows FSP1 staining in cranial suture, including suture mesenchyme, with in vivo CTGF delivery. b: bone; m: marrow; μs: microspheres. Scale: 200 μm.
FIG. 5C shows vimentin staining in cranial suture, including suture mesenchyme, without in vivo CTGF delivery. b: bone; m: marrow. Scale: 100 μm.
FIG. 5D shows vimentin staining in cranial suture, including suture mesenchyme, with in vivo CTGF delivery. b: bone; μs: microspheres. Scale: 200 μm. Diffused medium to dark grey areas (or black in lower left of FIG. 5D) correspond to FSP1 staining, but do not generally include dark grey granular structures. For additional details regarding methodology, see Example 14.

In contrast to localization of FSP1-positive cells in the marrow of synostosed bone of the representative placebo microsphere delivery specimen (see e.g., FIG. 5A), the representative CCN2/CTGF-mediated cranial suture was populated by abundant FSP1 positive cells (see e.g., FIG. 5B). Vimentin expression was scarce in the representative placebo microsphere delivery specimen (see e.g., FIG. 5C), in sharp contrast to strong and abundant vimentin positive cells in the representative CCN2/CTGF-mediated cranial suture (see e.g., FIG. 5D).

Thus CCN2/CTGF delivery yields substantial number of FSP1 and vimentin positive cells in suture mesenchyme.

Example 15

CCN2/CTGF Further Suppresses Osteogenesis In Vivo

Methods are according to those described in Examples 1-7 unless specified otherwise.

CTGF attenuates osteopontin and TGFβ2 expression in regenerated cranial suture, but not surrounding bone. Without in vivo CTGF delivery, TGFβ2 and osteopontin positive cells were broadly located in calvarial bone (see e.g., FIG. 6A, FIG. 6B), although suture mesenchyme is obliterated. Overlay of a and b indicates that TGFβ2 and osteopontin somewhat co-localized. Contrastingly, TGFβ2 and osteopontin positive cells were scarce in the regenerated cranial suture (see e.g., FIG. 6D, FIG. 6E). Overlay of d and e indicates that TGFβ2 and osteopontin co-localized in calvarial bone, but absent in the regenerated cranial suture (see e.g., FIG. 6F). Quantitatively, CTGF delivery significantly reduced TGFβ2 and osteopontin expression in the regenerated cranial suture (see e.g., FIG. 6G, FIG. 6H). However, TGFβ2 and osteopontin expression showed a lack of statistically significant differences in calvarial bone excluding the regenerated cranial suture (see e.g., FIG. 6I, FIG. 6J), suggesting that CTGF may have promoted selective differentiation of suture mesenchyme cells into fibroblastic, rather than osteoblastic, lineages.

Figures 6A, 6B, 6C, 6D, 6E, 6F:
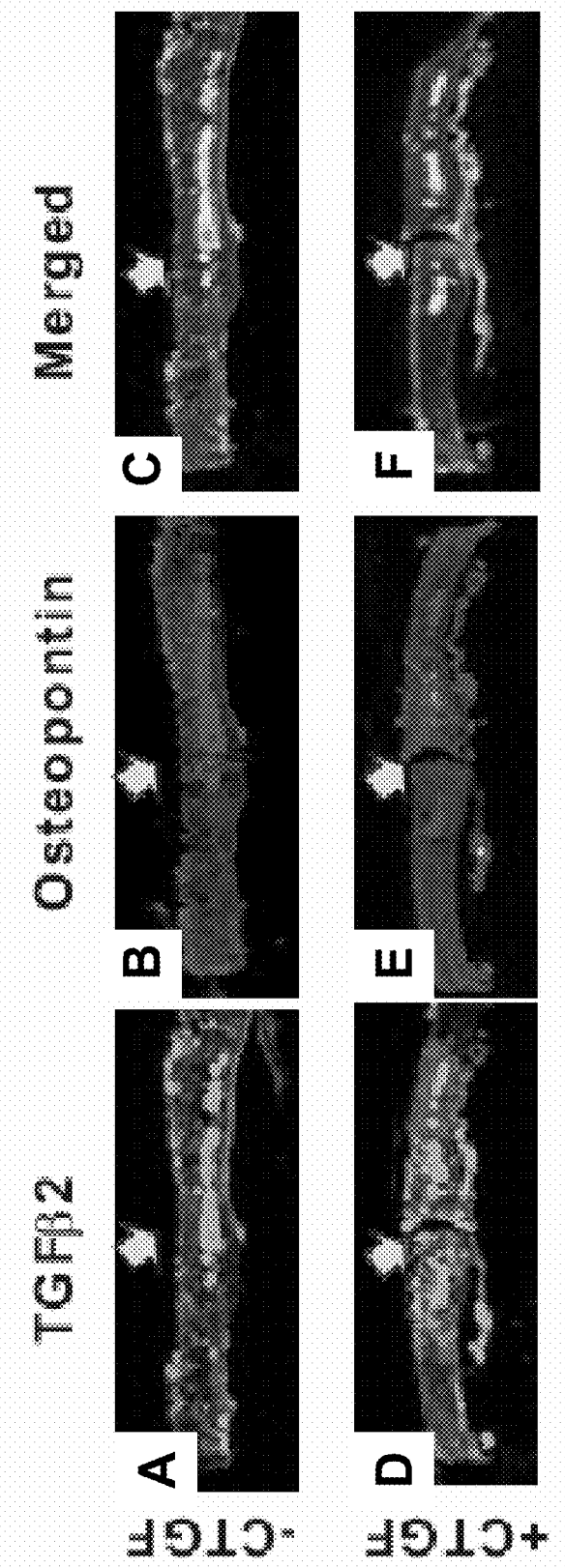
FIG. 6A is an immunofluorescence image showing cranial suture stained for TGFβ2 without CTGF treatment. White to medium grey areas correspond to TGFβ2 staining.
FIG. 6B is an immunofluorescence image showing cranial suture stained for osteopontin without CTGF treatment. Light to medium grey areas correspond to osteopontin staining.
FIG. 6C is a merged image of FIG. 6A and FIG. 6B.
FIG. 6D is an immunofluorescence image showing cranial suture stained for TGFβ2 with CTGF treatment. White to medium grey areas correspond to TGFβ2 staining.
FIG. 6F is a merged image of FIG. 6D and FIG. 6E. White arrow points to suture mesenchyme. For additional details regarding methodology, see Example 15.
Figures 6G, 6H, 6I, 6J:
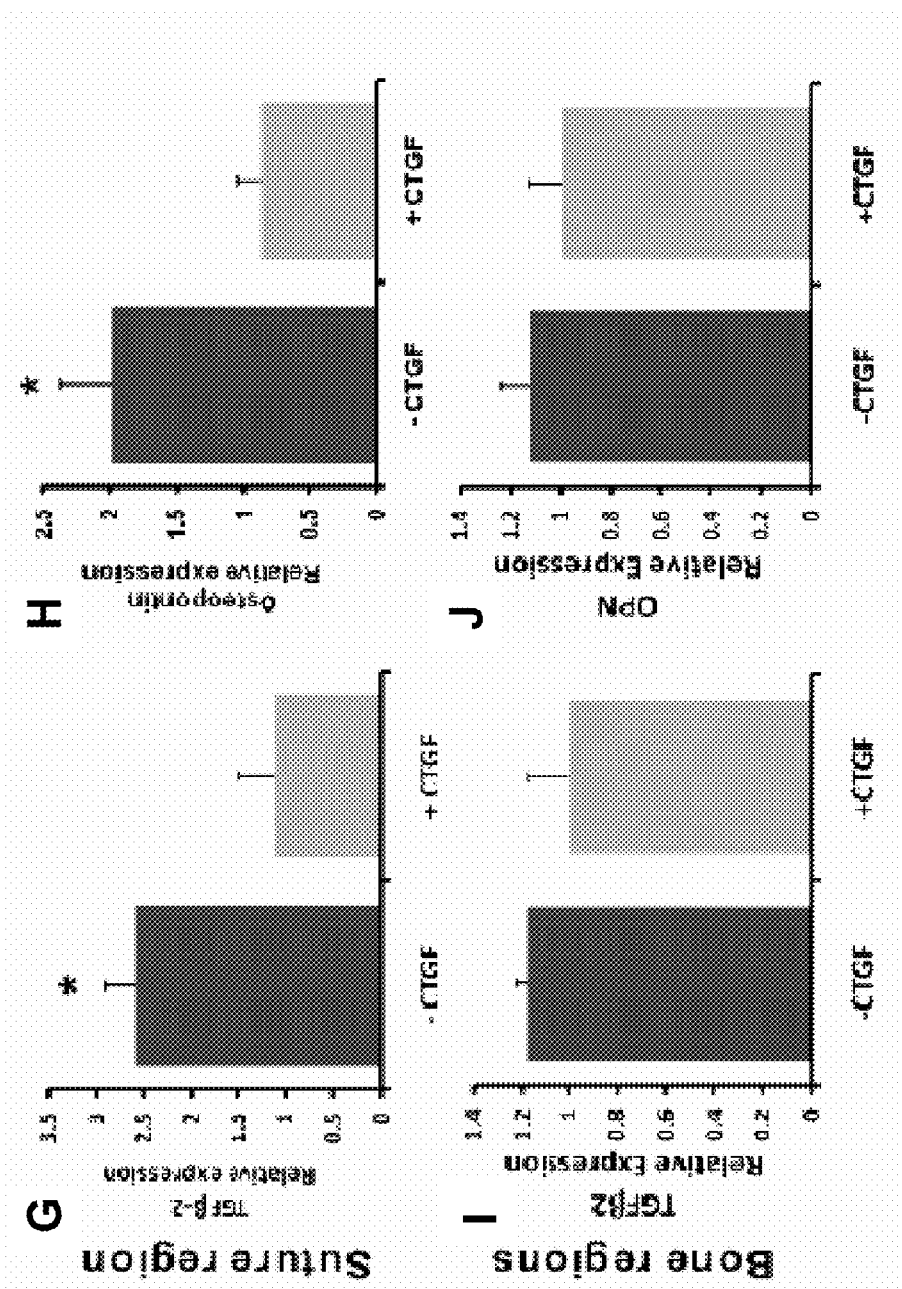
FIG. 6 is a series of immunofluorescence images and a series of bar graphs.

Without CCN2/CTGF delivery, TGFβ2 and osteopontin were broadly expressed in synostosed bone (see e.g., FIG. 6A, FIG. 6B). Superimposed images showed substantial co-localization of TGFβ2 and osteopontin expression (see e.g., FIG. 6C). In contrast, CCN2/CTGF-mediated, regenerated cranial suture showed little TGFβ2 and osteopontin expression in suture mesenchyme (see e.g., FIG. 6D, FIG. 6E). Again, TGFβ2 and osteopontin expression mostly co-localized (see e.g., FIG. 6F). Quantitatively, CCN2/CTGF significantly attenuated 2-2.5 fold TGFβ2 and osteopontin expression in regenerated cranial sutures as compared to cranial sutures without CCN2/CTGF delivery (see e.g., FIG. 6G, FIG. 6H). However, CCN2/CTGF failed to suppress either TGFβ2 or osteopontin expression in the rest of calvarial bone in comparison to without CCN2/CTGF delivery (p=0.37 and p=0.17, respectively) (n=5).

Thus CCN2/CTGF promotes fibrogenesis and suppresses osteogenesis in suture mesenchyme, but does not appear to suppress osteogenesis in calvarial bone.

Example 16

Isolation and Culture-Expansion of hMSCs

Human bone marrow samples taken from healthy donors ranging from 18 to 45 years of age were purchased from AllCells (Berkeley, Calif.). The bone marrows were prepared to isolate hMSCs per previous methods (Alhadlaq and Mao (2004) Stem Cells Dev. 13, 436-448; Marion ET AL. (2005) Mech. Adv. Mat. Struct. 12, 1-8). Briefly, the whole bone marrow sample was incubated with mesenchymal cell enrichment cocktail (RosetteSep™, StemCell Technologies, Inc., Vancouver, Canada). After incubation, the marrow sample was diluted with PBS containing 2% FBS and 1 mM EDTA. Diluted sample was then layered on top of a density gradient solution (Ficoll-Paque®; StemCell Technologies, Inc., Vancouver, Canada). Following centrifugation, enriched cells were removed and resuspended in cell culture media consisting of 89% DMEM, 10% FBS, and 1% penicillin-streptomycin (basal cell culture media). Cells were passaged up to two times each time upon confluency. Upon the second passage, the isolated hMSCs were grown in monolayer (5,000 cells/well) in 12-well culture plates in basal cell culture media, with fresh medium change every 3-4 days.

Example 17

Treatment of hMSCs with Connective Tissue Growth Factor

Upon near confluence, hMSCs were treated with DMEM supplemented with 0 and 100 ng/ml of recombinant human CTGF (BioVendor, Candler, N.C.) and 50 μg/ml ascorbic acid, with conditioned medium change every third day. Two to 4 weeks following CTGF and ascorbic acid treatment, the following molecular markers were assayed by ELISA: collagen type I (Chondrex, Redmond, Wash.) and tenascin-C (Tn-C; IBL-America, Minneapolis, Minn.), selected markers for ligament fibroblasts (Altman et al. (2002) FASEB J. 16, 270-272). The lysis of the selected extracellular matrix was performed using 0.5 M acetic acid solution. Collagen deposition was visualized using Trichrome staining.

Figures 7A, 7B:
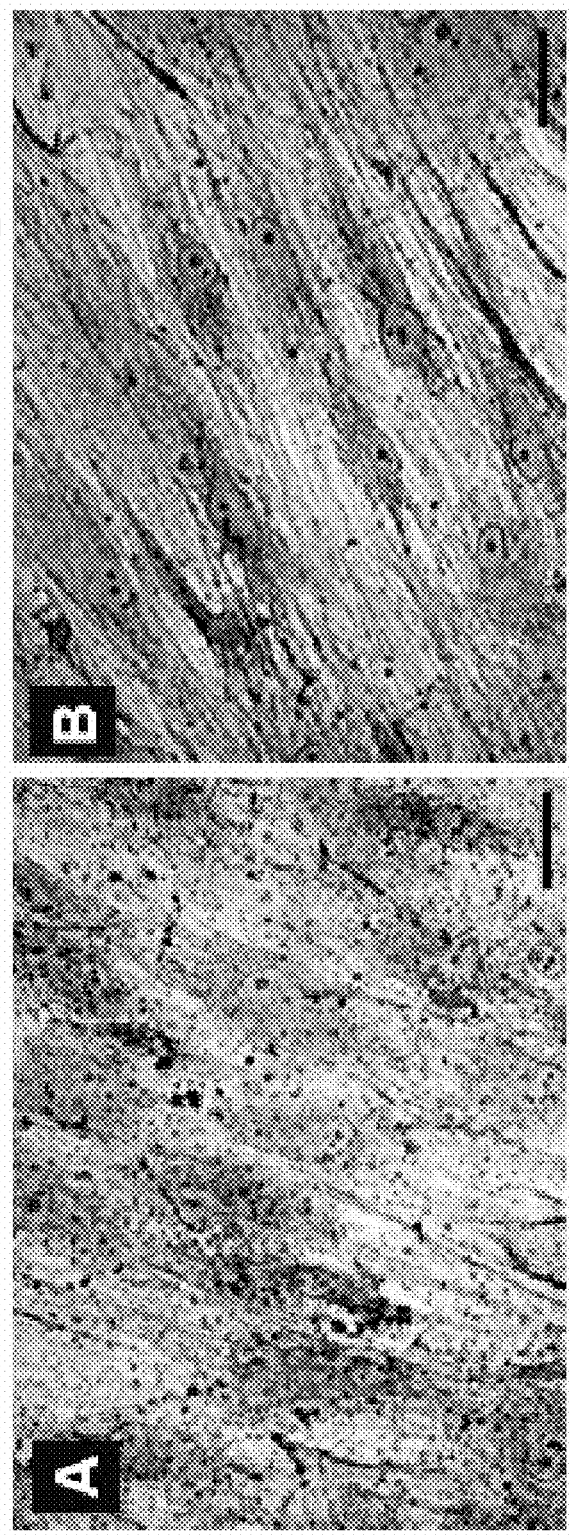
As shown in FIG. 7B, treatment with 100 ng/ml of CTGF induced an increase in collagen deposition (scale=50 μm). Further details regarding methodology are presented in Example 17.
Figure 8:
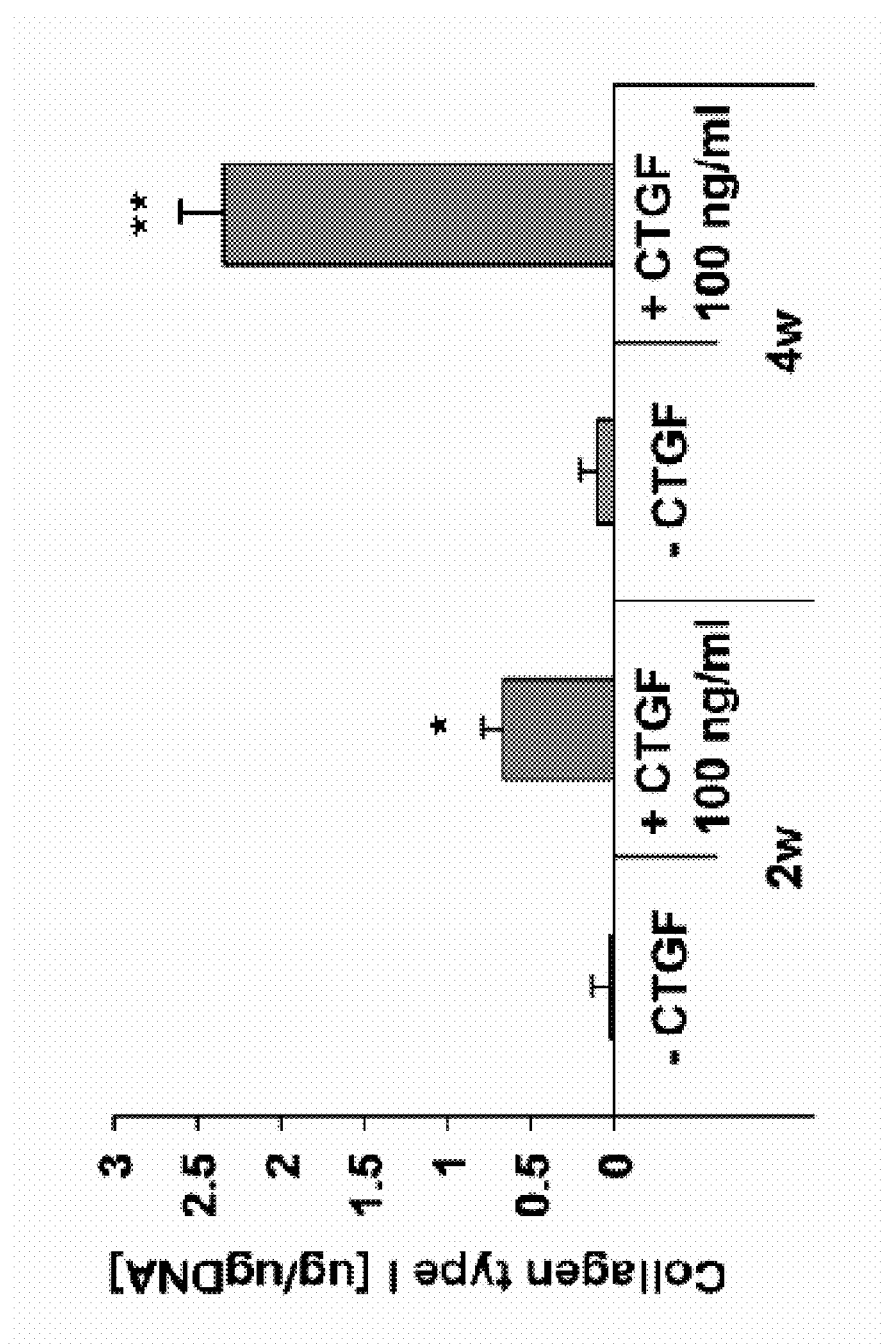
FIG. 8 is a bar graph depicting collagen type I contents with or without CTGF treatment. Type I collagen contents in monolayer cultured hMSCs were significantly increased by the treatment with 100 ng/ml CTGF and 50 μg/ml ascorbic acid by 2 & 4 wks (n=3, *: $p<0.01$, **: $p<0.001$). Further details regarding methodology are presented in Example 17.
Figure 9:
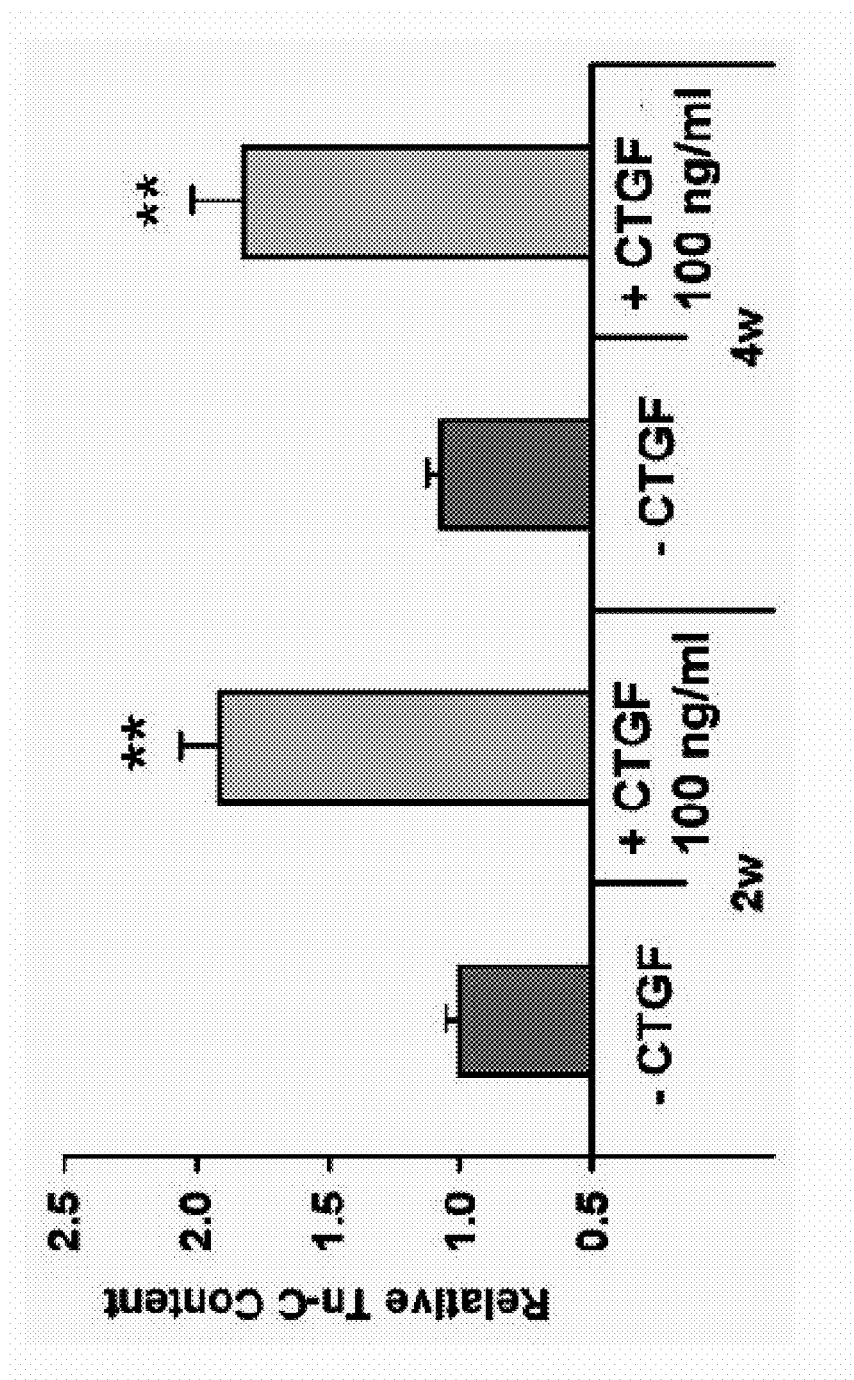
FIG. 9 is a series of images depicting Tn-C contents with CTGF treatment. Tn-C contents, a maker for ligament fibroblasts, were significantly increased by the treatment with 100 ng/ml CTGF and 50 μg/ml ascorbic acid by 2 & 4 wks (n=3, *: $p<0.01$, **: $p<0.001$). Further details regarding methodology are presented in Example 17.

Results showed that collagen and tenascin-C synthesis increases when hMSCs are treated with CTGF. Exposure of 100 ng/ml recombinant human CTGF and 50 μg/ml ascorbic acid to hMSCs induced remarkable increases in collagen deposition in 4 wks as revealed by Trichrome straining (see e.g., FIG. 7B), in comparison with hMSCs without CTGF and ascorbic acid supplements. These qualitative data were substantiated by quantitative analysis of collagen content. By 2 wks, collagen content of hMSCs treated with 100 ng/ml of CTGF increased significantly by approx. 4.5 fold in comparison with hMSCs without CTGF ($p<0.01$). By 4 wks, this increase was approx. 9.5 fold ($p<0.001$) (see e.g., FIG. 8). Tn-C content, another indication of fibroblastic differentiation, in hMSCs treated with CTGF was approx. 2 folds higher than hMSCs without CTGF by 2 wks (FIG. 9). By 4 wks of CTGF treatment, Tn-C content of hMSCs treated with CTGF remained approx. 1.8 folds higher than hMSCs without CTGF.

Figures 10A, 10B, 10C, 10D:
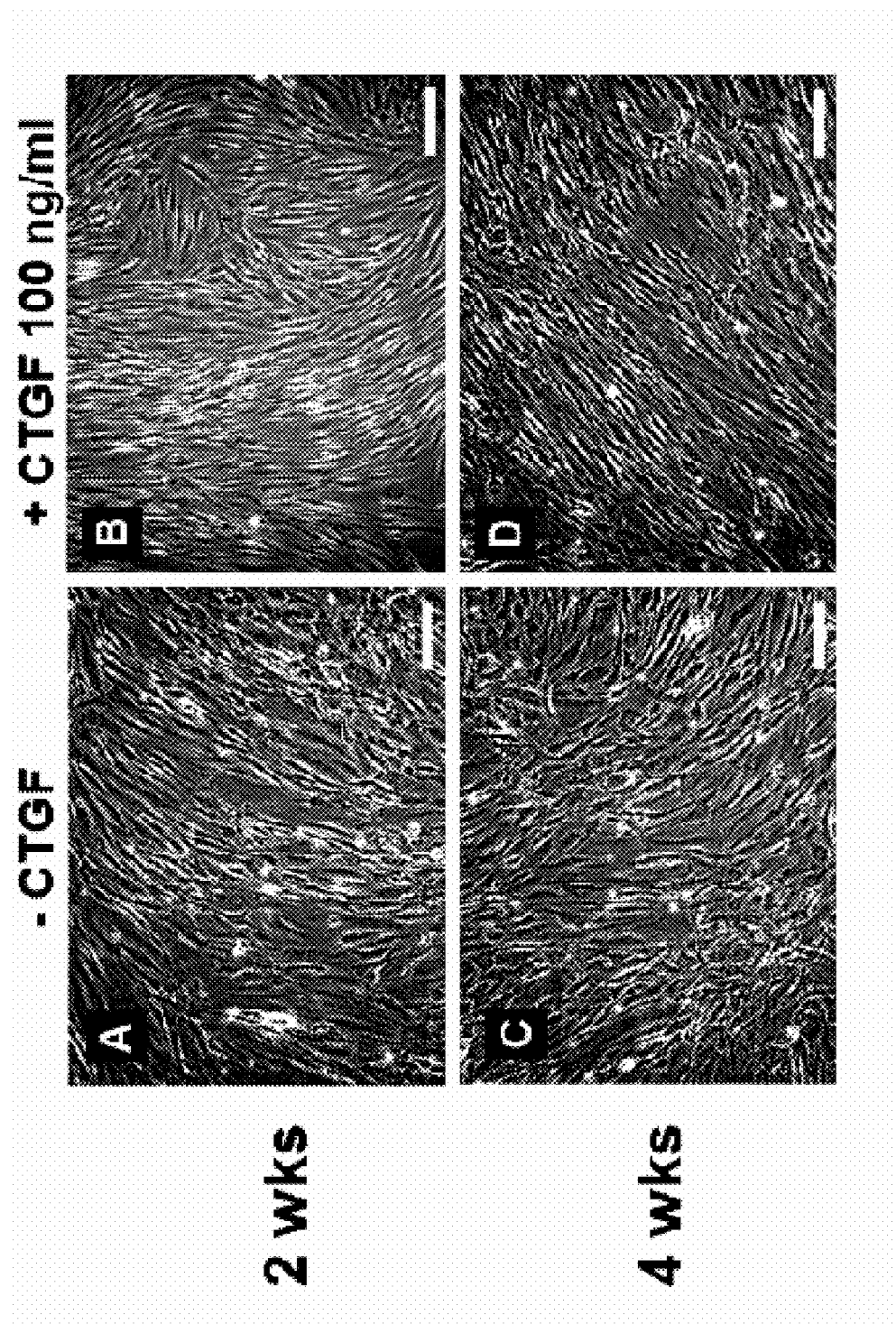
FIG. 10 is a series of images depicting morphology of hMSCs with (FIG. 10B, FIG. 10D) or without (FIG. 10A, FIG. 10C) CTGF treatment. Both hMSCs and CTGF-treated hMSCs showed fibroblast-like spindle shape. However, there were no significant differences in cellular morphology caused by CTGF-treatment by 2 (FIG. 10B) & 4 wks (FIG. 10D) (scale=200 μm). Further details regarding methodology are presented in Example 17.

Thus, the parallel increases in type I collagen and Tn-C contents suggest that hMSCs treated by CTGF have differentiated into cells that synthesize abundant type I collagen even though there were no significant changes in cellular morphology (see e.g., FIG. 10). However, one must at least rule out the possibility of osteogenic differentiation of these CTGF-treated hMSCs, given that osteoblasts also synthesize abundant type I collagen (see Example 18).

Example 18

Osteogenic and Chondrogenic Differentiation of hMSCs hMSCs were separately induced to differentiate into osteoblasts and chondrocytes to serve as controls for the above-described fibroblastic differentiation. Chondrogenic medium contained a supplement of 10 ng/ml TGF-β3 (R&D Systems Inc., Minneapolis, Minn.), whereas osteogenic medium contained 100 nM dexamethasone, 10 mM 6-glycerophosphate, and 0.05 mM ascorbic acid-2-phosphate (Sigma-Aldrich, St. Lois, Mo.) per prior methods with osteogenic or chondrogenic supplemented medium (Alhadlaq and Mao (2004) Stem Cells Dev. 13, 436-448; Marion et al. (2005) Mech. Adv. Mat. Struct. 12, 1-8). At Days 14 and 28, von Kossa staining and calcium content assay (Calcium reagents, Raichem, Columbia, Md.) were performed to evaluate osteogenic differentiation, whereas safranin O straining and glycosaminoglycan (GAG) assay were performed to evaluate chondrogenic differentiation (Blyscan™, Biocolor, UK).

Figures 11A, 11B, 11C:
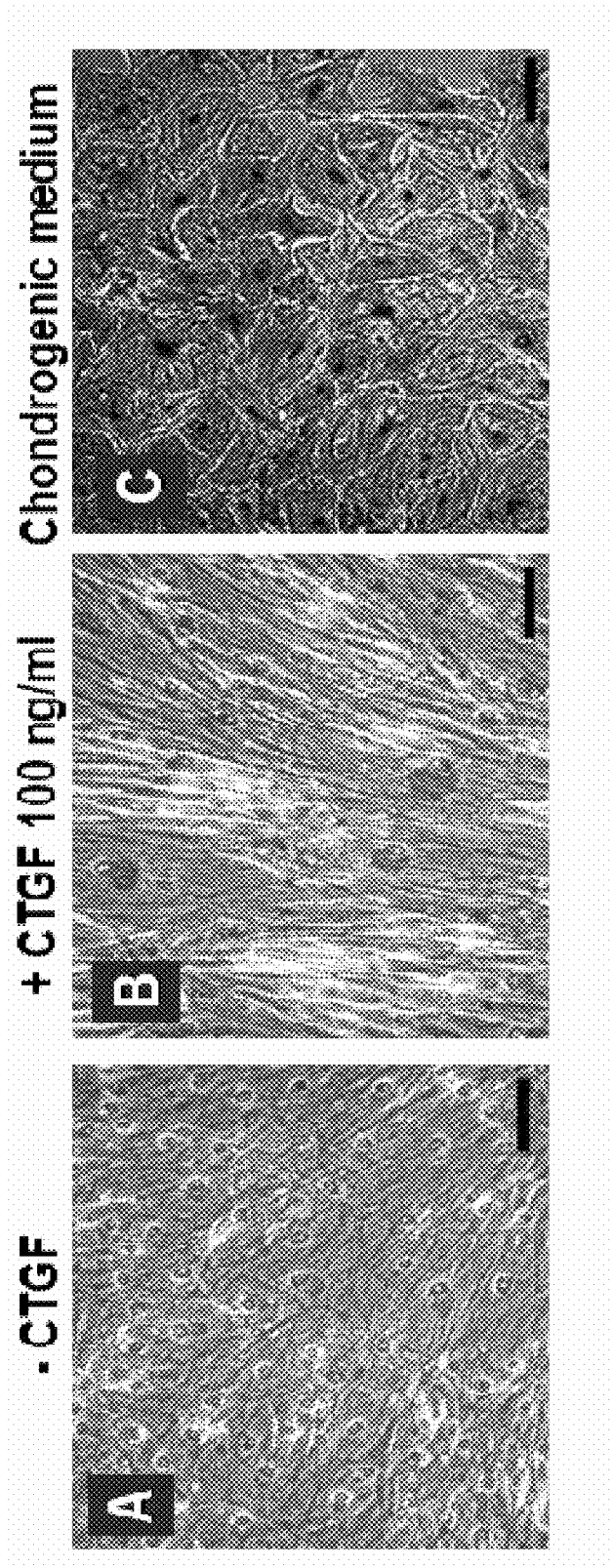
FIG. 11 is a series of images depicting safranin 0 staining of hMSCs treated without CTGF (FIG. 11A), with CTGF (FIG. 11B), and with chondrogenic medium (FIG. 11C) for 4 wks (scale=100 μm). Further details regarding methodology are presented in Example 18.
Figures 12A, 12B, 12C:
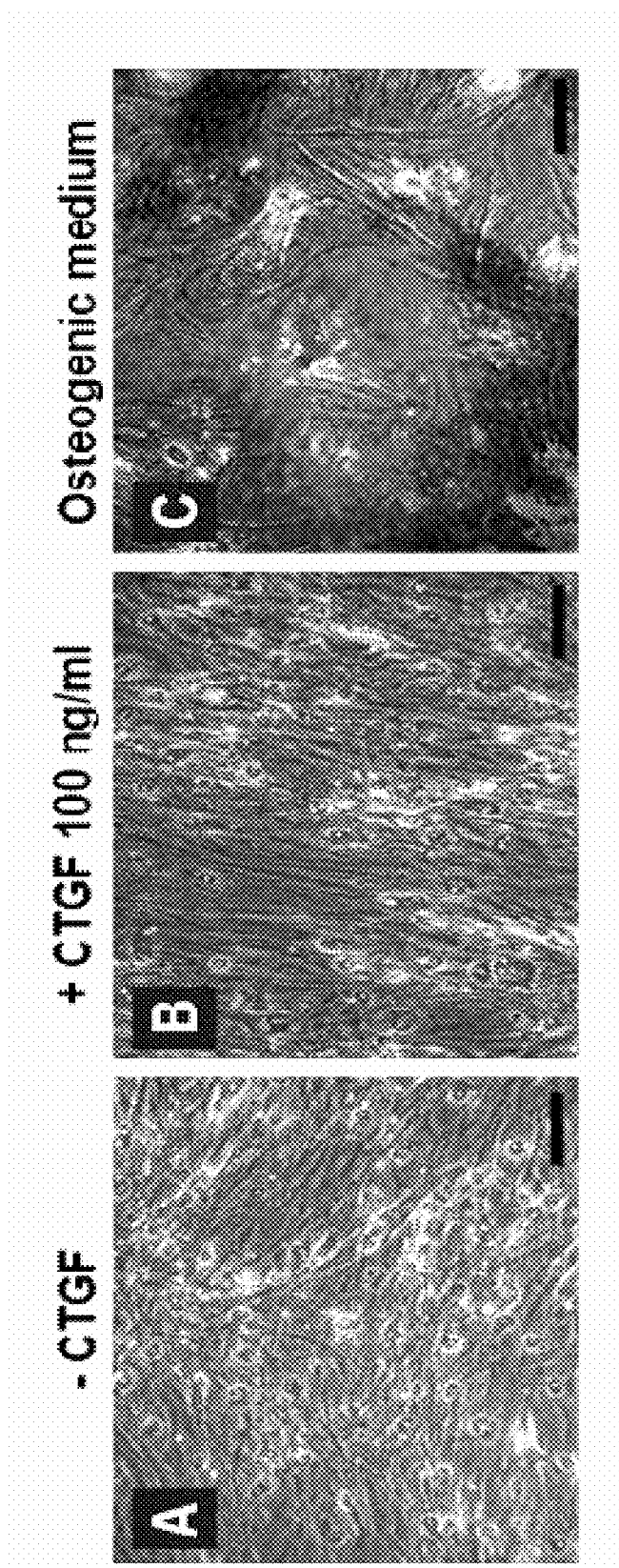
FIG. 12 is a series of images depicting von Kossa staining of hMSCs treated without CTGF (FIG. 12A), with CTGF (FIG. 12B), and with chondrogenic medium (FIG. 12C) for 4 wks (scale=100 μm). Further details regarding methodology are presented in Example 18.
Figure 13:
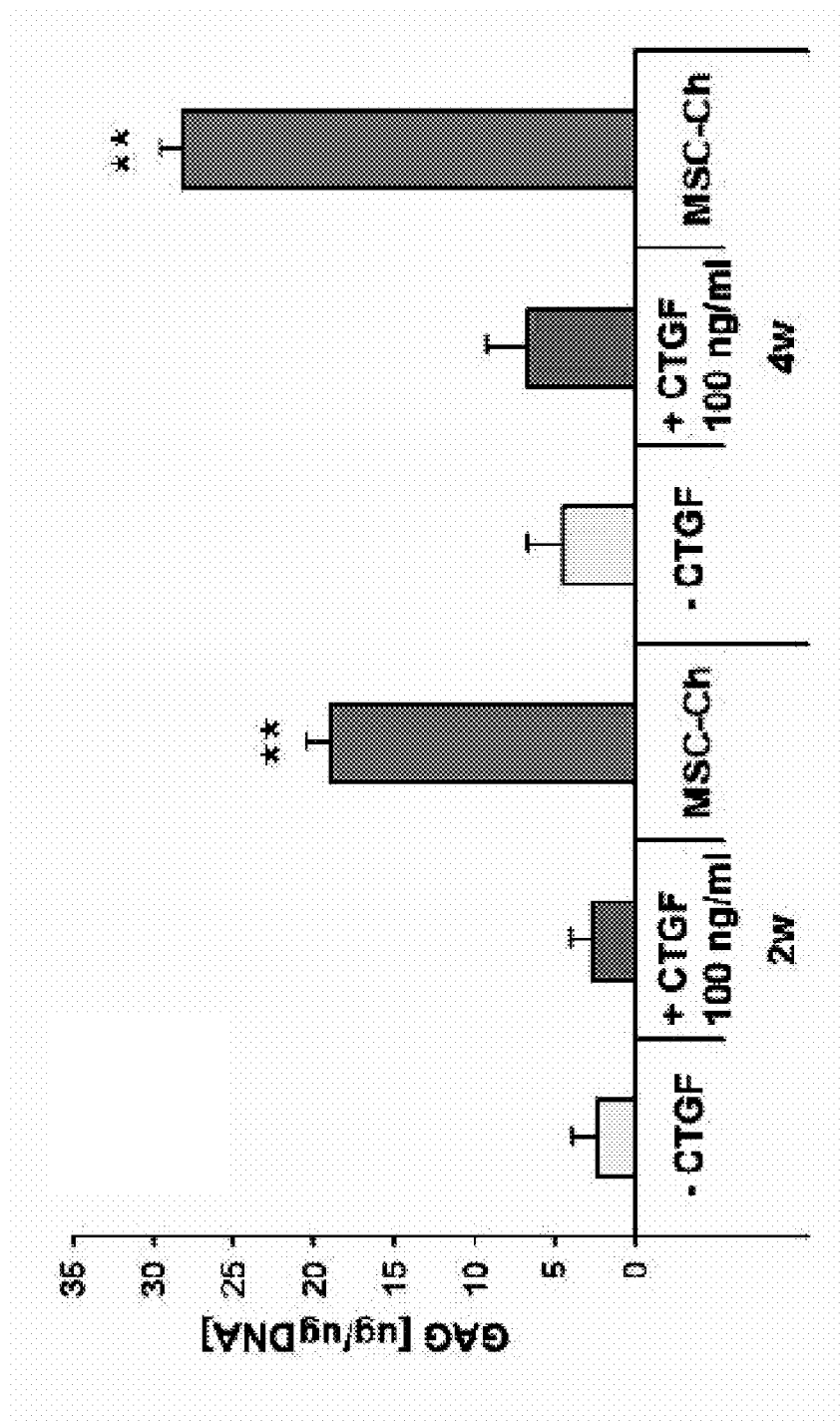
FIG. 13 is a series of bar graphs depicting GAG (FIG. 7A) and calcium deposition (FIG. 7B) in hMSCs monolayer treated with CTGF or corresponding differentiation medium. GAG content and calcium deposition were not affected by the treatment with 100 ng/ml of CTGF by 2 & 4 wks (n=3, *: $p<0.01$, **: $p<0.001$). Further details regarding methodology are presented in Example 18.

Results showed that CTGF-treated hMSCs fail to show osteogenic or chondrogenic differentiation. hMSCs cultured in chondrogenic or osteogenic supplemented medium showed corresponding chondrogenic or osteogenic differentiation (see e.g., FIG. 11C and FIG. 12C, respectively). However, neither hMSCs nor hMSCs treated with 100 ng/ml of CTGF showed any positive label of chondrogenic or osteogenic differentiation (see e.g., FIG. 11A; FIG. 11B; FIG. 12A; FIG. 12B). GAG content of hMSC-derived chondrocytes was significantly higher than hMSCs with or without CTGF (FIG. 13A). Calcium content of hMSC-derived osteoblasts was significantly higher than hMSCs with or without CTGF (FIG. 13B).

---

What is claimed is:

1. A method of treating a bone formation condition or disorder or an ectopic mineralization condition in a subject comprising:
administering to a tissue site of a subject in need thereof a therapeutically effective amount of a composition comprising connective tissue growth factor (CTGF);
wherein,
(a) the tissue site is associated with
(i) the bone formation condition or disorder, wherein the bone formation condition or disorder comprises a synostotic condition selected from the group consisting of synostitic sagittal synostosis, metopic synostosis, lambdoid synostosis, unilateral coronal synostosis, bicoronal synostosis, multiple suture synostosis, and syndromic craniosynostosis; or
(ii) the ectopic mineralization condition wherein the tissue site is a soft tissue site and the ectopic mineralization condition comprises an ectopic calcification condition selected from the group consisting of scleroderma, urethral stone, cardiac valve mineralization, and atherosclerosis, and
(b) the therapeutically effective amount of the composition delays ossification at the tissue site.

2. The method of claim 1 wherein the tissue site is a soft tissue site and the ectopic mineralization condition comprises an ectopic calcification condition selected from the group consisting of scleroderma, urethral stone, cardiac valve mineralization, and atherosclerosis.

3. The method of claim 1 wherein the bone formation condition or disorder comprises a synostotic condition selected from the group consisting of synostitic sagittal synostosis, metopic synostosis, lambdoid synostosis, unilateral coronal synostosis, bicoronal synostosis, multiple suture synostosis, and syndromic craniosynostosis.

4. The method of claim 1 wherein:
the bone formation condition or disorder comprises craniosynostosis; and
the tissue site comprises a cranial suture of the subject.

5. The method of claim 4 further comprising the step of accessing a cranial suture of the subject.

6. The method of claim 1 wherein administering the composition results in at least one of (i) promotion of fibroblast differentiation, (ii) inhibition of osteoblast differentiation, or (iii) promotion of fibroblast differentiation and inhibition of osteoblast differentiation.

7. The method of claim 1 wherein the composition further comprises at least one: of a transforming growth factor beta (TGFβ); a basic fibroblast growth factor (bFGF); a bone morphogenetic protein (BMP); a vascular endothelial growth factor (VEGF); an osteoprotegerin; and a periostin polypeptide.

8. The method of claim 1 wherein administration comprises injection in, at, or near the tissue site of the subject.

9. The method of claim 1 wherein the composition comprises CTGF in a concentration of at least about 0.1 ng/ml to about 100 mg/ml.

10. The method of claim 1 wherein the composition comprises CTGF in a concentration of about 50 ng/ml.

11. The method of claim 1 wherein the composition is administered via a carrier delivery system.

12. The method of claim 11 wherein the composition is encapsulated in a polymeric microsphere.

13. The method of claim 12 wherein the composition is encapsulated in a polymeric microsphere at a ratio of about 250 mg polymer to about 10 μg of CTGF.

14. The method of claim 12 wherein:
the tissue site comprises a cranial suture; and
administering the composition comprises introducing a collagen sponge comprising about 5 mg to about 15 mg of CTGF-encapsulated microspheres to the cranial suture.

15. The method of claim 1 wherein the composition further comprises at least one of a pharmaceutically acceptable carrier or excipient; an immunosuppressive agent; and an antibiotic.

16. The method of claim 1 wherein administering the composition comprises transforming a host cell to express SEQ ID NO: 1, or a polypeptide having at least about 95% sequence identity thereto and CTGF activity; introducing the transformed host cell to the tissue site; and expressing the encoded polypeptide having CTGF activity at or near the tissue site.

17. The method of claim 1 wherein administering the composition comprises:
introducing to the tissue site a construct comprising a polynucleotide of SEQ ID NO: 2, or a polynucleotide having at least about 95% sequence identity thereto and encoding a polypeptide having CTGF activity, operably linked to a promoter; and
expressing the encoded polypeptide having CTGF activity at or near the tissue site.

18. The method of claim 1 further comprising the step of administering a fibroblast cell to the tissue site of the subject.

19. The method of claim 1 further comprising the step of administering a progenitor cell to the tissue site of the subject and inducing progenitor cell differentiation to a fibroblast cell by contacting the progenitor cell with CTGF.

20. A method of delaying ossification of synostosing cranial sutures comprising administering a composition comprising connective tissue growth factor (CTGF) to a cranial suture of a subject in need thereof.

* * * * *

SEQUENCE LISTING

<160> NUMBER OF SEQ ID NOS: 2

<210> SEQ ID NO 1
<211> LENGTH: 2358
<212> TYPE: DNA
<213> ORGANISM: Homo sapiens
<220> FEATURE:
<221> NAME/KEY: CDS
<222> LOCATION: (207)..(1256)

<400> SEQUENCE: 1

```
aaactcacac aacaactctt ccccgctgag aggagacagc cagtgcgact ccaccctcca      60
gctcgacggc agccgccccg gccgacagcc ccgagacgac agcccggcgc gtcccggtcc     120
ccacctccga ccaccgccag cgctccaggc cccgccgctc cccgctcgcc gccaccgcgc     180
cctccgctcc gcccgcagtg ccaacc atg acc gcc gcc agt atg ggc ccc gtc     233
                              Met Thr Ala Ala Ser Met Gly Pro Val
                               1               5 cgc gtc gcc ttc gtg gtc ctc ctc gcc ctc tgc agc cgg ccg gcc gtc     281
Arg Val Ala Phe Val Val Leu Leu Ala Leu Cys Ser Arg Pro Ala Val
 10                  15                  20                  25 ggc cag aac tgc agc ggg ccg tgc cgg tgc ccg gac gag ccg gcg ccg     329
Gly Gln Asn Cys Ser Gly Pro Cys Arg Cys Pro Asp Glu Pro Ala Pro
                 30                  35                  40 cgc tgc ccg gcg ggc gtg agc ctc gtg ctg gac ggc tgc ggc tgc tgc     377
Arg Cys Pro Ala Gly Val Ser Leu Val Leu Asp Gly Cys Gly Cys Cys
             45                  50                  55 cgc gtc tgc gcc aag cag ctg ggc gag ctg tgc acc gag cgc gac ccc     425
Arg Val Cys Ala Lys Gln Leu Gly Glu Leu Cys Thr Glu Arg Asp Pro
         60                  65                  70 tgc gac ccg cac aag ggc ctc ttc tgt gac ttc ggc tcc ccg gcc aac     473
Cys Asp Pro His Lys Gly Leu Phe Cys Asp Phe Gly Ser Pro Ala Asn
     75                  80                  85 cgc aag atc ggc gtg tgc acc gcc aaa gat ggt gct ccc tgc atc ttc     521
Arg Lys Ile Gly Val Cys Thr Ala Lys Asp Gly Ala Pro Cys Ile Phe
 90                  95                 100                 105 ggt ggc acg gtg tac cgc agc gga gag tcc ttc cag agc agc tgc aag     569
Gly Gly Thr Val Tyr Arg Ser Gly Glu Ser Phe Gln Ser Ser Cys Lys
                110                 115                 120 tac cag tgc acg tgc ctg gac ggg gcg gtg ggc tgc atg ccc ctg tgc     617
Tyr Gln Cys Thr Cys Leu Asp Gly Ala Val Gly Cys Met Pro Leu Cys
```

```
                     125                 130                 135
agc atg gac gtt cgt ctg ccc agc cct gac tgc ccc ttc ccg agg agg          665
Ser Met Asp Val Arg Leu Pro Ser Pro Asp Cys Pro Phe Pro Arg Arg
        140                 145                 150 gtc aag ctg ccc ggg aaa tgc tgc gag gag tgg gtg tgt gac gag ccc          713
Val Lys Leu Pro Gly Lys Cys Cys Glu Glu Trp Val Cys Asp Glu Pro
155                 160                 165 aag gac caa acc gtg gtt ggg cct gcc ctc gcg gct tac cga ctg gaa          761
Lys Asp Gln Thr Val Val Gly Pro Ala Leu Ala Ala Tyr Arg Leu Glu
170                 175                 180                 185 gac acg ttt ggc cca gac cca act atg att aga gcc aac tgc ctg gtc          809
Asp Thr Phe Gly Pro Asp Pro Thr Met Ile Arg Ala Asn Cys Leu Val
                190                 195                 200 cag acc aca gag tgg agc gcc tgt tcc aag acc tgt ggg atg ggc atc          857
Gln Thr Thr Glu Trp Ser Ala Cys Ser Lys Thr Cys Gly Met Gly Ile
                205                 210                 215 tcc acc cgg gtt acc aat gac aac gcc tcc tgc agg cta gag aag cag          905
Ser Thr Arg Val Thr Asn Asp Asn Ala Ser Cys Arg Leu Glu Lys Gln
            220                 225                 230 agc cgc ctg tgc atg gtc agg cct tgc gaa gct gac ctg gaa gag aac          953
Ser Arg Leu Cys Met Val Arg Pro Cys Glu Ala Asp Leu Glu Glu Asn
        235                 240                 245 att aag aag ggc aaa aag tgc atc cgt act ccc aaa atc tcc aag cct          1001
Ile Lys Lys Gly Lys Lys Cys Ile Arg Thr Pro Lys Ile Ser Lys Pro
250                 255                 260                 265 atc aag ttt gag ctt tct ggc tgc acc agc atg aag aca tac cga gct          1049
Ile Lys Phe Glu Leu Ser Gly Cys Thr Ser Met Lys Thr Tyr Arg Ala
                270                 275                 280 aaa ttc tgt gga gta tgt acc gac ggc cga tgc tgc acc ccc cac aga          1097
Lys Phe Cys Gly Val Cys Thr Asp Gly Arg Cys Cys Thr Pro His Arg
                285                 290                 295 acc acc acc ctg ccg gtg gag ttc aag tgc cct gac ggc gag gtc atg          1145
Thr Thr Thr Leu Pro Val Glu Phe Lys Cys Pro Asp Gly Glu Val Met
                300                 305                 310 aag aag aac atg atg ttc atc aag acc tgt gcc tgc cat tac aac tgt          1193
Lys Lys Asn Met Met Phe Ile Lys Thr Cys Ala Cys His Tyr Asn Cys
        315                 320                 325 ccc gga gac aat gac atc ttt gaa tcg ctg tac tac agg aag atg tac         1241
Pro Gly Asp Asn Asp Ile Phe Glu Ser Leu Tyr Tyr Arg Lys Met Tyr
330                 335                 340                 345 gga gac atg gca tga agccagagag tgagagacat taactcatta gactggaact          1296
Gly Asp Met Ala tgaactgatt cacatctcat ttttccgtaa aaatgatttc agtagcacaa gttatttaaa        1356
tctgtttttc taactggggg aaaagattcc cacccaattc aaaacattgt gccatgtcaa        1416
acaaatagtc tatcaacccc agacactggt ttgaagaatg ttaagacttg acagtggaac       1476
tacattagta cacagcacca gaatgtatat taaggtgtgg ctttaggagc agtgggaggg       1536
taccagcaga aaggttagta tcatcagata gcatcttata cgagtaatat gcctgctatt       1596
tgaagtgtaa ttgagaagga aaattttagc gtgctcactg acctgcctgt agccccagtg       1656
acagctagga tgtgcattct ccagccatca agagactgag tcaagttgtt ccttaagtca       1716
gaacagcaga ctcagctctg acattctgat tcgaatgaca ctgttcagga atcggaatcc      1776
tgtcgattag actggacagc ttgtggcaag tgaatttgcc tgtaacaagc cagattttt       1836 aaaatttata ttgtaaatat tgtgtgtgtg tgtgtgtgtg tatatatata tatatgtaca       1896
gttatctaag ttaatttaaa gttgtttgtg ccttttatt tttgttttta atgctttgat       1956
```

-continued

```
atttcaatgt tagcctcaat ttctgaacac cataggtaga atgtaaagct tgtctgatcg    2016
ttcaaagcat gaaatggata cttatatgga aattctgctc agatagaatg acagtccgtc    2076
aaaacagatt gtttgcaaag gggaggcatc agtgtccttg gcaggctgat ttctaggtag    2136
gaaatgtggt agcctcactt ttaatgaaca aatggccttt attaaaaact gagtgactct    2196
atatagctga tcagtttttt cacctggaag catttgtttc tactttgata tgactgtttt    2256
tcggacagtt tatttgttga gagtgtgacc aaaagttaca tgtttgcacc tttctagttg    2316
aaaataaagt gtatatttt tctataaaaa aaaaaaaaa aa                        2358
```

<210> SEQ ID NO 2
<211> LENGTH: 349
<212> TYPE: PRT
<213> ORGANISM: Homo sapiens

<400> SEQUENCE: 2

```
Met Thr Ala Ala Ser Met Gly Pro Val Arg Val Ala Phe Val Val Leu
1               5                   10                  15

Leu Ala Leu Cys Ser Arg Pro Ala Val Gly Gln Asn Cys Ser Gly Pro
                20                  25                  30

Cys Arg Cys Pro Asp Glu Pro Ala Pro Arg Cys Pro Ala Gly Val Ser
            35                  40                  45

Leu Val Leu Asp Gly Cys Gly Cys Cys Arg Val Cys Ala Lys Gln Leu
    50                  55                  60

Gly Glu Leu Cys Thr Glu Arg Asp Pro Cys Asp Pro His Lys Gly Leu
65                  70                  75                  80

Phe Cys Asp Phe Gly Ser Pro Ala Asn Arg Lys Ile Gly Val Cys Thr
                85                  90                  95

Ala Lys Asp Gly Ala Pro Cys Ile Phe Gly Gly Thr Val Tyr Arg Ser
            100                 105                 110

Gly Glu Ser Phe Gln Ser Ser Cys Lys Tyr Gln Cys Thr Cys Leu Asp
        115                 120                 125

Gly Ala Val Gly Cys Met Pro Leu Cys Ser Met Asp Val Arg Leu Pro
    130                 135                 140

Ser Pro Asp Cys Pro Phe Pro Arg Arg Val Lys Leu Pro Gly Lys Cys
145                 150                 155                 160

Cys Glu Glu Trp Val Cys Asp Glu Pro Lys Asp Gln Thr Val Val Gly
                165                 170                 175

Pro Ala Leu Ala Ala Tyr Arg Leu Glu Asp Thr Phe Gly Pro Asp Pro
            180                 185                 190

Thr Met Ile Arg Ala Asn Cys Leu Val Gln Thr Thr Glu Trp Ser Ala
        195                 200                 205

Cys Ser Lys Thr Cys Gly Met Gly Ile Ser Thr Arg Val Thr Asn Asp
    210                 215                 220

Asn Ala Ser Cys Arg Leu Glu Lys Gln Ser Arg Leu Cys Met Val Arg
225                 230                 235                 240

Pro Cys Glu Ala Asp Leu Glu Glu Asn Ile Lys Lys Gly Lys Lys Cys
                245                 250                 255

Ile Arg Thr Pro Lys Ile Ser Lys Pro Ile Lys Phe Glu Leu Ser Gly
            260                 265                 270

Cys Thr Ser Met Lys Thr Tyr Arg Ala Lys Phe Cys Gly Val Cys Thr
        275                 280                 285

Asp Gly Arg Cys Cys Thr Pro His Arg Thr Thr Thr Leu Pro Val Glu
    290                 295                 300
```

-continued

```
Phe Lys Cys Pro Asp Gly Glu Val Met Lys Lys Asn Met Met Phe Ile
305                 310                 315                 320

Lys Thr Cys Ala Cys His Tyr Asn Cys Pro Gly Asp Asn Asp Ile Phe
                325                 330                 335

Glu Ser Leu Tyr Tyr Arg Lys Met Tyr Gly Asp Met Ala
            340                 345
```